(12) United States Patent
Lecomte et al.

(10) Patent No.: US 10,980,648 B1
(45) Date of Patent: Apr. 20, 2021

(54) VARIABLE STIFFNESS MECHANISM AND LIMB SUPPORT DEVICE INCORPORATING THE SAME

(71) Applicant: Össur Iceland ehf, Reykjavik (IS)

(72) Inventors: Christophe Guy Lecomte, Reykjavik (IS); Felix Starker, Reykjavik (IS); Heimir Tryggvason, Reykjavik (IS)

(73) Assignee: Össur Iceland ehf, Reykjavik (IS)

( * ) Notice: Subject to any disclaimer, the term of this patent is extended or adjusted under 35 U.S.C. 154(b) by 126 days.

(21) Appl. No.: 16/132,004

(22) Filed: Sep. 14, 2018

Related U.S. Application Data

(60) Provisional application No. 62/559,338, filed on Sep. 15, 2017.

(51) Int. Cl.
| | | |
|---|---|---|
| *A61F 2/66* | (2006.01) | |
| *A61F 2/74* | (2006.01) | |
| *A61F 2/68* | (2006.01) | |
| A61F 2/50 | (2006.01) | |
| A61F 2/30 | (2006.01) | |

(52) U.S. Cl.
CPC .. *A61F 2/6607* (2013.01); *A61F 2002/30014* (2013.01); *A61F 2002/503* (2013.01); *A61F 2002/5004* (2013.01); *A61F 2002/6657* (2013.01); *A61F 2002/6863* (2013.01); *A61F 2002/745* (2013.01)

(58) Field of Classification Search
CPC .. A61F 2/60; A61F 2/66; A61F 2/6607; A61F 2/68; A61F 2/76; A61F 2002/5001–5006
See application file for complete search history.

(56) References Cited

U.S. PATENT DOCUMENTS

| 25,238 A | 8/1859 | Bly |
|---|---|---|
| 53,931 A | 4/1866 | Weston |
| 56,983 A | 8/1866 | Nicholas |
| 57,666 A | 9/1866 | Bly |

(Continued)

FOREIGN PATENT DOCUMENTS

| CA | 2 234 362 | 10/1998 |
|---|---|---|
| CN | 1196917 | 10/1998 |

(Continued)

OTHER PUBLICATIONS

Burden et al., "Numerical Analysis", Second Edition, Review of Calculus, Section 1.1, 1981, Prindle, Weber & Schmidt, p. 3.

(Continued)

*Primary Examiner* — Marcia L Watkins
(74) *Attorney, Agent, or Firm* — Knobbe, Martens, Olson & Bear, LLP

(57) ABSTRACT

A limb support device includes a variable stiffness mechanism. The limb support device can be an orthotic or prosthetic device. The variable stiffness mechanism can include, for example, a rate-sensitive or speed-dependent material or a damping mechanism. The variable stiffness mechanism causes the limb support device to exhibit different properties when the user of the limb support device is walking at high or fast walking speeds compared to low or slow walking speeds. The limb support device can exhibit high damping and energy absorption, and therefore stability, at slow speeds, and high energy return at faster speeds.

20 Claims, 22 Drawing Sheets

(56) References Cited

U.S. PATENT DOCUMENTS

| | | |
|---|---|---|
| 368,580 A | 8/1887 | Frees |
| 487,697 A | 12/1892 | Ehle |
| 534,198 A | 2/1895 | Chapman |
| 619,731 A | 2/1899 | Doerflinger et al. |
| 808,296 A | 12/1905 | Merrick |
| 809,876 A | 1/1906 | Wilkins |
| 817,340 A | 4/1906 | Rosenkranz |
| 2,183,076 A | 12/1939 | Kaiser |
| 2,197,093 A | 4/1940 | Campbell |
| 2,315,795 A | 4/1943 | Johnson et al. |
| 2,357,893 A | 9/1944 | Harrington |
| 2,594,945 A | 4/1952 | Lucas et al. |
| 2,692,392 A | 10/1954 | Bennington et al. |
| 2,731,645 A | 1/1956 | Woodall |
| 3,551,914 A | 1/1971 | Woodall |
| 3,784,988 A | 1/1974 | Trumpler |
| 3,874,004 A | 4/1975 | May |
| 4,007,497 A | 2/1977 | Haupt |
| 4,360,931 A | 11/1982 | Hampton |
| 4,387,472 A | 6/1983 | Wilson |
| 4,547,913 A | 10/1985 | Phillips |
| 4,636,220 A | 1/1987 | Ziegelmeyer |
| 4,718,913 A | 1/1988 | Voisin |
| 4,822,363 A | 4/1989 | Phillips |
| 4,892,553 A | 1/1990 | Prahl |
| 4,892,554 A | 1/1990 | Robinson |
| 4,959,073 A | 9/1990 | Merlette |
| 5,019,109 A | 5/1991 | Voisin |
| 5,037,444 A | 8/1991 | Phillips |
| 5,062,859 A | 11/1991 | Naeder |
| 5,112,356 A | 5/1992 | Harris et al. |
| 5,116,384 A | 5/1992 | Wilson et al. |
| 5,139,525 A | 8/1992 | Kristinsson |
| 5,156,631 A | 10/1992 | Merlette |
| 5,181,932 A | 1/1993 | Phillips |
| 5,181,933 A | 1/1993 | Phillips |
| 5,219,365 A | 6/1993 | Sabolich |
| 5,258,039 A | 11/1993 | Goh et al. |
| 5,290,319 A | 3/1994 | Phillips |
| 5,376,133 A | 12/1994 | Gramnaes |
| 5,376,141 A | 12/1994 | Phillips |
| 5,387,246 A | 2/1995 | Phillips |
| 5,443,527 A | 8/1995 | Wilson |
| 5,443,529 A | 8/1995 | Phillips |
| 5,509,938 A | 4/1996 | Phillips |
| 5,545,234 A | 8/1996 | Collier, Jr. |
| 5,571,210 A | 11/1996 | Lindh |
| 5,653,767 A | 8/1997 | Allen et al. |
| 5,701,686 A | 12/1997 | Herr et al. |
| 5,728,177 A | 3/1998 | Phillips |
| 5,800,589 A | 9/1998 | Phillips |
| 5,888,239 A | 3/1999 | Wellershaus et al. |
| 5,897,594 A | 4/1999 | Martin et al. |
| 5,899,944 A | 5/1999 | Phillips |
| 5,913,901 A | 6/1999 | Lacroix |
| 5,941,913 A | 8/1999 | Woolnough et al. |
| 5,957,981 A | 9/1999 | Gramnaes |
| 5,993,488 A | 11/1999 | Phillips |
| 6,071,313 A | 6/2000 | Phillips |
| 6,099,572 A | 8/2000 | Mosler et al. |
| 6,129,766 A | 10/2000 | Johnson et al. |
| 6,165,227 A | 12/2000 | Phillips |
| 6,206,934 B1 | 3/2001 | Phillips |
| 6,241,776 B1 | 6/2001 | Christensen |
| 6,261,324 B1 | 7/2001 | Merlette |
| 6,280,479 B1 | 8/2001 | Phillips |
| 6,350,286 B1 | 2/2002 | Atkinson et al. |
| 6,387,134 B1 | 5/2002 | Parker et al. |
| 6,398,818 B1 | 6/2002 | Merlette et al. |
| 6,402,790 B1 | 6/2002 | Celebi |
| 6,443,993 B1 | 9/2002 | Koniuk |
| 6,443,995 B1 | 9/2002 | Townsend et al. |
| 6,562,075 B2 | 5/2003 | Townsend et al. |
| 6,596,029 B1 | 7/2003 | Gramnäs |
| 6,663,673 B2 | 12/2003 | Christensen |
| 6,712,860 B2 | 3/2004 | Rubie et al. |
| 6,719,807 B2 | 4/2004 | Harris |
| 6,767,370 B1 | 7/2004 | Mosler et al. |
| 6,793,683 B1 | 9/2004 | Laghi |
| 6,855,170 B2 | 2/2005 | Gramnäs |
| 6,899,737 B1 | 5/2005 | Phillips |
| 6,942,704 B2 | 9/2005 | Sulprizio |
| 6,969,408 B2 | 11/2005 | Lecomte et al. |
| 7,029,500 B2 | 4/2006 | Martin |
| 7,052,519 B1 | 5/2006 | Gramnäs |
| 7,341,603 B2 | 3/2008 | Christensen |
| 7,347,877 B2 | 3/2008 | Clausen et al. |
| 7,507,259 B2 | 3/2009 | Townsend et al. |
| 7,520,904 B2 | 4/2009 | Christensen |
| 7,578,852 B2 | 8/2009 | Townsend et al. |
| 7,727,285 B2 | 6/2010 | Christensen et al. |
| 7,763,082 B1 | 7/2010 | Curtis |
| 7,766,974 B2 | 8/2010 | Curtis |
| 7,862,622 B2 | 1/2011 | Dunlap et al. |
| 7,942,935 B2 * | 5/2011 | Iversen ............ A61F 2/70 623/25 |
| 8,007,544 B2 | 8/2011 | Jonsson et al. |
| 8,025,699 B2 | 9/2011 | Lecomte et al. |
| 8,246,695 B2 | 8/2012 | Mosler |
| 8,317,876 B2 | 11/2012 | Mosler |
| 8,377,144 B2 | 2/2013 | Jonsson et al. |
| 8,574,313 B2 | 11/2013 | Clausen et al. |
| 8,764,850 B2 | 7/2014 | Hanset et al. |
| 8,814,949 B2 | 8/2014 | Gramnaes |
| 8,888,864 B2 | 11/2014 | Iversen et al. |
| 8,915,969 B2 * | 12/2014 | Boender ............ F16F 9/512 623/26 |
| 9,366,306 B2 * | 6/2016 | Miyasato ............ F16F 9/20 |
| 9,427,338 B2 | 8/2016 | Clausen et al. |
| 2002/0013628 A1 | 1/2002 | Harris |
| 2002/0040249 A1 | 4/2002 | Phillips |
| 2002/0087216 A1 | 7/2002 | Atkinson et al. |
| 2002/0116072 A1 | 8/2002 | Rubie et al. |
| 2002/0143408 A1 | 10/2002 | Townsend et al. |
| 2002/0183860 A1 | 12/2002 | Wilkinson |
| 2003/0093158 A1 | 5/2003 | Phillips et al. |
| 2003/0120353 A1 | 6/2003 | Christensen |
| 2004/0064195 A1 | 4/2004 | Herr |
| 2004/0068327 A1 | 4/2004 | Christensen |
| 2004/0122529 A1 | 6/2004 | Townsend et al. |
| 2004/0162623 A1 | 8/2004 | Phillips |
| 2004/0181289 A1 | 9/2004 | Bédard et al. |
| 2004/0225376 A1 | 11/2004 | Townsend et al. |
| 2005/0038524 A1 | 2/2005 | Jonsson et al. |
| 2005/0038525 A1 | 2/2005 | Doddroe et al. |
| 2005/0107889 A1 | 5/2005 | Bédard et al. |
| 2005/0137717 A1 | 6/2005 | Gramnaes |
| 2005/0267603 A1 | 12/2005 | Lecomte et al. |
| 2006/0069450 A1 | 3/2006 | McCarvill et al. |
| 2006/0235545 A1 | 10/2006 | Habecker |
| 2007/0027557 A1 | 2/2007 | Jonsson et al. |
| 2009/0204229 A1 | 8/2009 | Mosley et al. |
| 2009/0222105 A1 | 9/2009 | Clausen |
| 2013/0218297 A1 | 8/2013 | Nordman, Jr. et al. |
| 2014/0249652 A1 | 9/2014 | Taszreak |
| 2015/0257902 A1 * | 9/2015 | Martin ............ A61F 2/6607 623/52 |
| 2015/0328020 A1 | 11/2015 | Clausen et al. |
| 2015/0351938 A1 * | 12/2015 | Moser ............ A61F 2/6607 623/26 |
| 2016/0008147 A1 | 1/2016 | Marlin |
| 2016/0033053 A1 * | 2/2016 | Battlogg ............ F16K 31/0675 251/129.01 |
| 2016/0310298 A1 | 10/2016 | Jonsson et al. |
| 2017/0049584 A1 | 2/2017 | Pusch et al. |
| 2017/0128236 A1 | 5/2017 | Meyer et al. |
| 2018/0153712 A1 | 6/2018 | Albertsson et al. |

FOREIGN PATENT DOCUMENTS

| | | |
|---|---|---|
| DE | 817 186 | 10/1951 |
| DE | 834 884 | 3/1952 |
| DE | 832 473 | 4/1952 |

(56) References Cited

FOREIGN PATENT DOCUMENTS

| | | |
|---|---|---|
| DE | 838 480 | 5/1952 |
| DE | 924 230 | 2/1955 |
| DE | 1 491 182 | 7/1969 |
| DE | 1 941 762 | 3/1971 |
| DE | 298 20 904 | 4/1999 |
| DE | 299 12 832 | 12/2000 |
| EP | 0 401 864 | 9/1989 |
| EP | 0 940 129 | 11/1992 |
| EP | 0 648 479 | 4/1995 |
| EP | 1 149 568 | 10/2001 |
| EP | 2 944 290 | 11/2015 |
| FR | 661 071 | 7/1929 |
| FR | 1 213 026 | 3/1960 |
| FR | 2 658 717 | 8/1991 |
| GB | 117547 | 8/1918 |
| GB | 120462 | 11/1918 |
| GB | 621576 | 4/1949 |
| GB | 625528 | 6/1949 |
| GB | 1 371 996 | 10/1974 |
| KR | 2000-0000930 | 1/2000 |
| KR | 2000-0002059 | 1/2000 |
| KR | 2000-0047310 | 7/2000 |
| KR | 2001-0055393 | 7/2001 |
| KR | 2002-0041137 | 6/2002 |
| SE | 9400380-3 | 8/1995 |
| SU | 1454449 | 1/1989 |
| SU | 1600759 | 10/1990 |
| SU | 1700759 | 12/1991 |
| WO | WO 88/006431 | 9/1988 |
| WO | WO 93/004645 | 3/1993 |
| WO | WO 94/018914 | 9/1994 |
| WO | WO 96/004869 | 2/1996 |
| WO | WO 98/053769 | 12/1998 |
| WO | WO 99/052476 | 10/1999 |
| WO | WO 00/027317 | 5/2000 |
| WO | WO 01/006965 | 2/2001 |
| WO | WO 02/002034 | 1/2002 |
| WO | WO 02/051342 | 7/2002 |
| WO | WO 2004/032809 | 4/2004 |
| WO | WO 2005/048887 | 6/2005 |
| WO | WO 2011/066354 | 6/2011 |

OTHER PUBLICATIONS

Commercial Ad for College Park Venture Prosthetic Foot; http://www.college-park.com/assets/pdf/VentureInfoSheets.pdf, © 2003, www.college-park.com/CPStore/ProducInfoVenture.asp; available before Aug. 15, 2003 in 4 pages.

Freedom Innovations FS2000 LP product; http://www.freedom-innovations.com/product_details.asp?seriesid=1&prodid=2, © 2003; available before Aug. 15, 2003, 1 page.

Freedom Innovations Runway Product; http://www.freedom-innovations.com/product_details.asp?seriesid=2&prodid=11, © 2004; available before Dec. 18, 2003 in 1 page.

Ohio Willow Wood Company: Carbon Copy System III brochure available before May 2004, 5 pages.

ÖSSUR Allurion product; http://www.ossur.com/template1.asp?pageid=84 and product catalog pp. 146-149; available before Aug. 15, 2003 in 5 Total pages.

ÖSSUR Elation product; http://www.ossur.com/template1.asp?pageid=263 and product catalog pp. 193-196; available before Aug. 15, 2003.

ÖSSUR Total Concept Product, ÖSSUR Products Catalog, 2001-2002, pp. 243-249.

Otto Bock—Axtion product; http://www.ottobockus.com/products/lower_limb_prosthetics/axtion.asp; believed to have been released May 2004.

The Quantum Foot (Hosmer Dorrance Corporation), Circa 1988, 4 pages.

The Quantum Foot Brochure (Technical Information), Early 1989, 6 pages.

Merlette et al., "The Springlite Foot, The Design Process for a Novel Advanced Composite Prosthesis", Composites in Manufacturing: Case Studies, Society of Manufacturing Engineers, 1991, pp. 269-288.

* cited by examiner

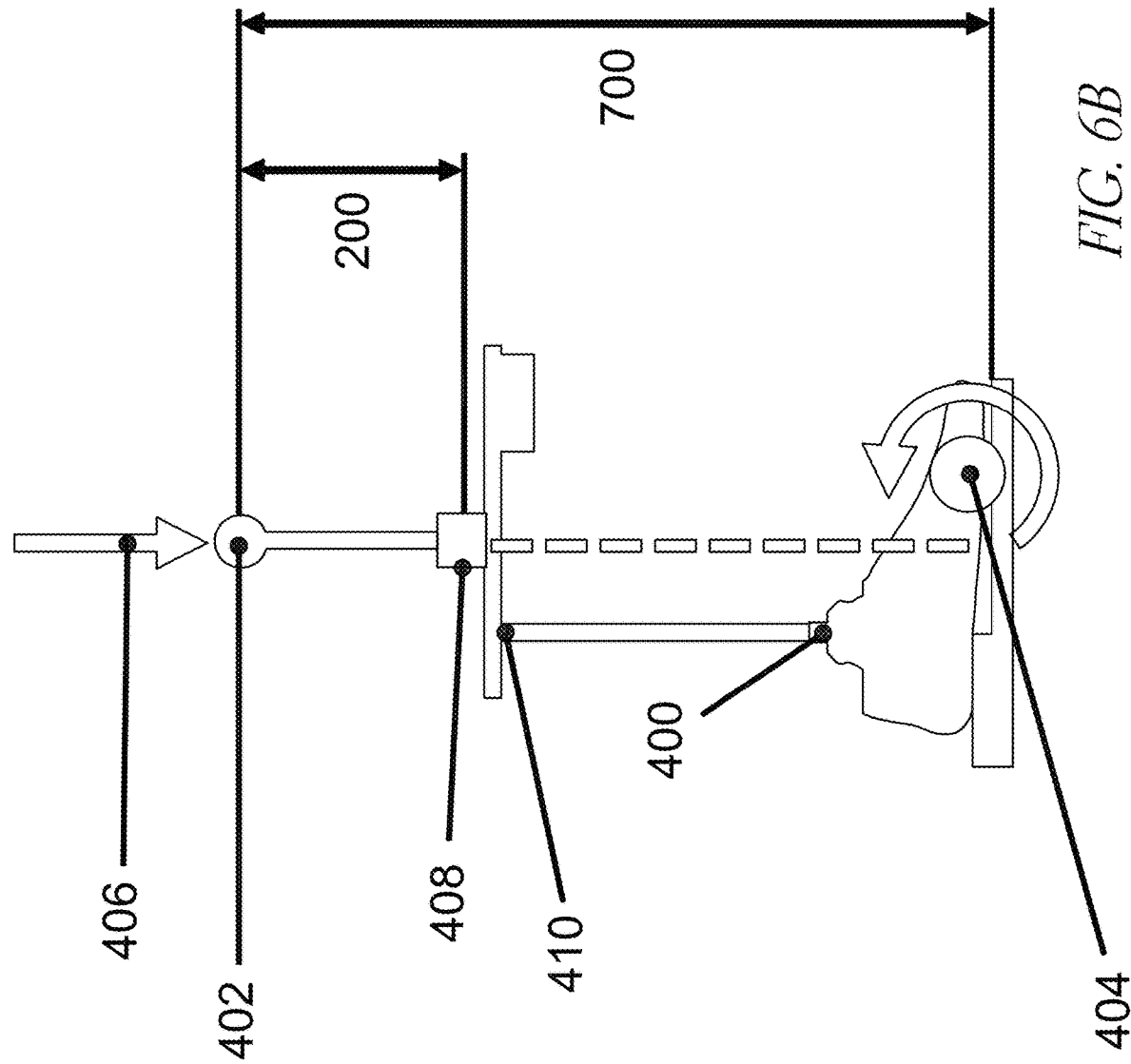

VARIABLE STIFFNESS MECHANISM AND LIMB SUPPORT DEVICE INCORPORATING THE SAME

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims the priority benefit of U.S. Provisional Application No. 62/559,338, filed Sep. 15, 2017, the entirety of which is incorporated herein by reference.

BACKGROUND

Field

The present application relates to variable stiffness mechanisms, for example, for a limb support device such as orthotic or prosthetic devices, for example prosthetic feet.

Description of the Related Art

In the field of prosthetics, particularly prosthetic feet, it is desirable to provide a high level of functionality with reliable performance. Some existing passive prosthetic feet are made of low energy returning materials such as wood or polyurethane foams. Such feet do not provide significant energy return at higher or faster walking speeds and do not allow for an energy efficient gait pattern. Some existing passive prosthetic feet are made of higher energy returning materials such as carbon fiber. Such feet can provide a greater energy return, closer to an ideal spring, which can allow a more energy efficient gait at higher walking speeds, for example, greater than around 3 km/h. However, such high energy return feet may provide more limited stability at slower walking speeds, for example, less than around 3 km/h. Some existing electronically controlled and actuated prosthetic feet are able to vary the ankle joint angle of the prosthetic foot and generate a net positive energy push-off force during use. However, such feet may have increased weight compared to passive prosthetic feet due to the energy source and actuator.

SUMMARY

In accordance with one aspect, a limb support device includes a variable stiffness mechanism. The limb support device can be an orthotic or prosthetic device. The variable stiffness mechanism can include, for example, a rate-sensitive or speed-dependent material or a damping mechanism. The variable stiffness mechanism causes the limb support device to exhibit different properties when the user of the limb support device is walking at high or fast walking speeds compared to low or slow walking speeds. The limb support device can exhibit high damping and energy absorption, and therefore stability, at slow speeds, and high energy return at faster speeds.

In some embodiments, a prosthetic foot includes an attachment member, a first flexible member, a second flexible member, and a link. The attachment member comprises a connector configured to connect the attachment member to a user or another prosthetic device. The first flexible member extends from a proximal end to a distal end, the proximal end connected to the attachment member. The second flexible member extends from a proximal end to a distal end. The link extends between and connects the proximal end of the second flexible member and the attachment member. The link comprises a variable stiffness mechanism, wherein a stiffness of the variable stiffness mechanism varies based on a gait speed of the user.

The prosthetic foot can further include a third flexible member coupled to the first and second flexible members. The proximal end of the first flexible member can be rotatably connected to the attachment member.

The variable stiffness mechanism can be or include one or more of: a magnetorheologic damper, a magnetorheologic brake, an electroadhesive brake, a fluid damper, a damper and a spring, and electrorheologic damper, an electro-active damper, and electro-active polymer, a piezo-electric material (such as a piezo-electric polymer foam), an electret, one or more elastic spring elements, a speed-dependent material, a non-Newtonian material, and/or a shear thickening material or fluid.

The variable stiffness mechanism can act in one or both of compression and extension. The variable stiffness mechanism can be adjustable for both compression and extension. The variable stiffness mechanism can act in compression and extension independently with different characteristics for extension vs. compression.

In some embodiments, a lower limb support device includes an attachment member, a first flexible member, a second flexible member, and a link. The attachment member is configured to operably connect to a lower limb of a user. The first flexible member extends from a proximal end to a distal end, the proximal end connected to the attachment member. The second flexible member extends from a proximal end to a distal end. The link extends between and connects the proximal end of the second flexible member and the attachment member. The link comprises a variable stiffness mechanism, wherein a stiffness of the variable stiffness mechanism varies based on a gait speed of the user.

In some embodiments, the lower limb support device is a prosthetic foot. The attachment member can include a pyramid connector. The lower limb support device can further include a third flexible member coupled to the first and second flexible members. The proximal end of the first flexible member can be rotatably connected to the attachment member.

The variable stiffness mechanism can be or include one or more of: a magnetorheologic damper, a magnetorheologic brake, an electroadhesive brake, a fluid damper (such as using a shear thickening fluid), a damper and a spring, and electrorheologic damper, an electro-active damper, and electro-active polymer, a piezo-electric material (such as a piezo-electric polymer foam), an electret, one or more elastic spring elements, a speed-dependent material, a non-Newtonian material, and/or a shear thickening material or fluid.

The variable stiffness mechanism can act in one or both of compression and extension. The variable stiffness mechanism can be adjustable (e.g., independently adjustable) for both compression and extension. The variable stiffness mechanism can act in compression and extension independent with different characteristics for extension vs. compression.

In some embodiments, a prosthetic foot can comprise an attachment member comprising a connector configured to connect the attachment member to a user or another prosthetic device; a first flexible member extending from a proximal end to a distal end, the proximal end connected to the attachment member; a second flexible member extending from a proximal end to a distal end; and an actuator extending between and connecting the proximal end of the second flexible member and the attachment member. The actuator can comprise a cylinder having sealed openings on two ends of the cylinder and a piston at least partially enclosed within the cylinder and defining a pair of chambers within the cylinder on opposite sides of the piston. The piston can be configured to translate along a longitudinal axis of a cylinder. The piston can be operably coupled to the proximal end of the second flexible member and the attachment member. The actuator can further comprise a volume of shear thickening fluid disposed in on or both of the chambers within the cylinder the shear thickening fluid configured to pass from one chamber to the other chamber via one or more orifices in the piston or cylinder as the piston moves within the cylinder. A stiffness of the shear thickening fluid can vary based on a gait speed of the user.

A rod can extend through the piston and can be coupled to the proximal end of the second flexible member at a first end of the rod and to the attachment member at an opposite second end of the rod. The rod can comprise a first portion coupled to the attachment member and a second portion coupled to the proximal end of the second flexible member. The sealed openings can be configured to slidably accommodate the rod. The piston can be entirely enclosed within the cylinder. The piston can be partially enclosed within the cylinder, the actuator further comprising an accumulator to account for a volume change of fluid-filled space when the piston is moved relative to the cylinder. The shear thickening fluid can have a higher apparent viscosity at a higher gait speed than at a lower gait speed. The shear thickening fluid can have a critical shear rate between $10 \text{ s}^{-1}$ and $80 \text{ s}^{-1}$. The foot can further comprise a third flexible member coupled to the first and second flexible members. The proximal end of the first flexible member can be rotatably connected to the attachment member. The proximal end of the first flexible member can be connected to the attachment member at a location more anterior than a connection location between the actuator and the attachment member. The attachment member can comprise a pyramid connector.

BRIEF DESCRIPTION OF THE DRAWINGS

These and other features, aspects, and advantages of the invention disclosed herein are described below with reference to the drawings of preferred embodiments, which are intended to illustrate and not to limit the invention. Additionally, from figure to figure, the same reference numerals have been used to designate the same components of an illustrated embodiment. The following is a brief description of each of the drawings.

FIG. 6B shows the equipment set up for a mechanical testing of the prosthetic foot.

DETAILED DESCRIPTION

A natural human ankle varies its stiffness based on the activity being performed by the user, such as walking at various speeds, rising to stand from a seated position, sitting down, ascending and descending stairs, walking on uneven terrain, and/or running. The ankle can vary between, for example, relatively low stiffness and relatively high damping during slow walking, which can allow for easier transitions, and relatively higher stiffness and relatively lower damping when walking at faster speeds, which can provide greater energy efficiency. Some currently available prosthetic feet are adapted for either high damping, e.g., via a hydraulic mechanism, or high energy efficiency, e.g., via carbon fiber leaf springs. However, such prosthetic feet typically have fixed damping and/or spring characteristics optimized for a particular gait speed on level ground and may not adapt well to other speeds or activities. While prosthetic feet including an electric motor in series with a spring arrangement can allow for some variable stiffness, such prosthetic feet may lack desirable damping behavior during some activities. Passive hydraulic damping systems may continuously increase the energy expended during a gait cycle in favor of allowing for a greater range of ankle motion. The prosthetic feet described herein include variable stiffness mechanisms and/or properties. Such mechanisms can allow the foot to continuously fade or adapt between relatively high damping with relatively low stiffness and relatively low damping with relatively high stiffness. The foot can therefore adapt to varying walking speeds and activities.

Figure 1A:
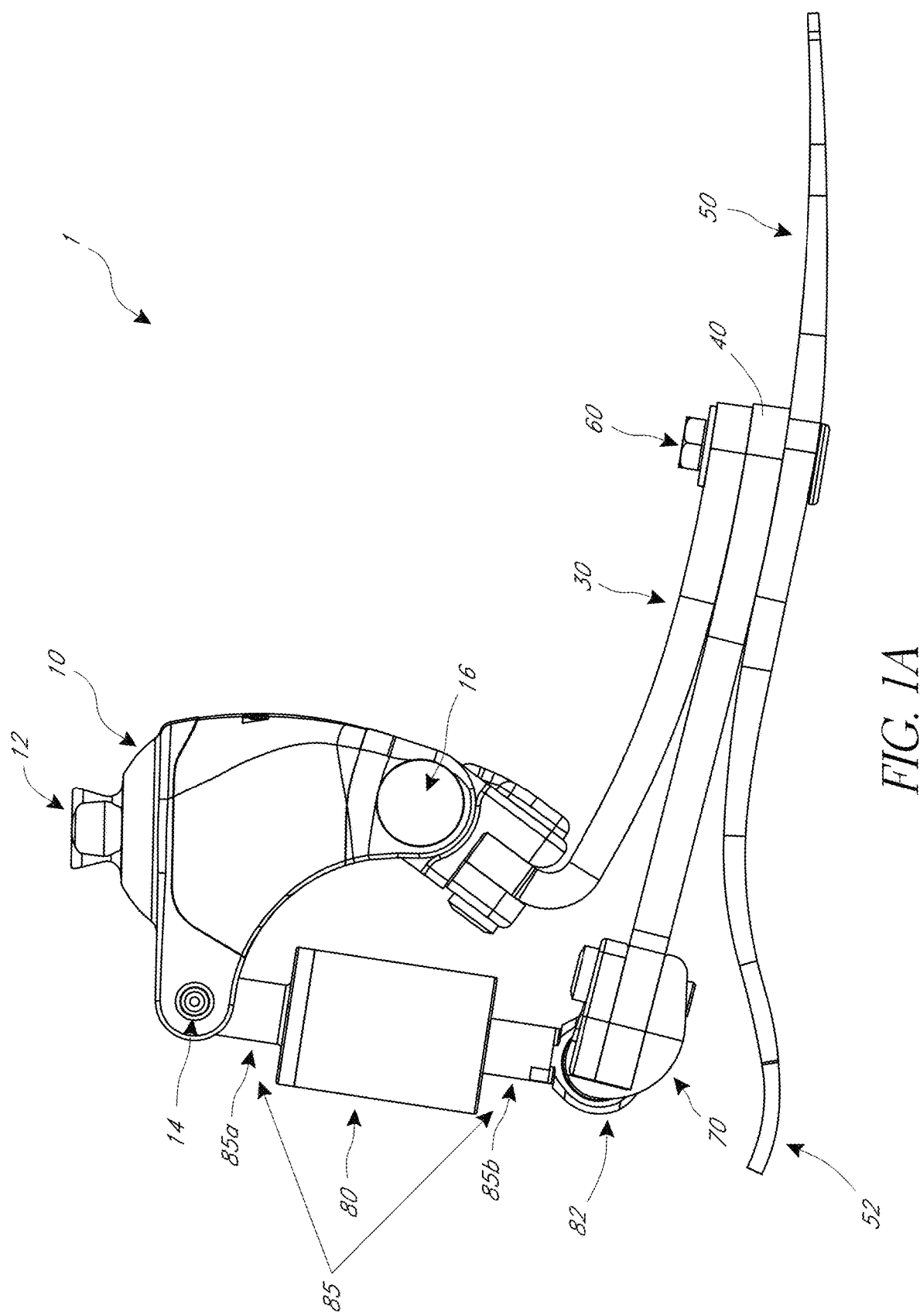
FIG. 1A is a side view of an embodiment of a prosthetic foot having a sheer thickening fluid (STF) actuator.
Figure 1B:
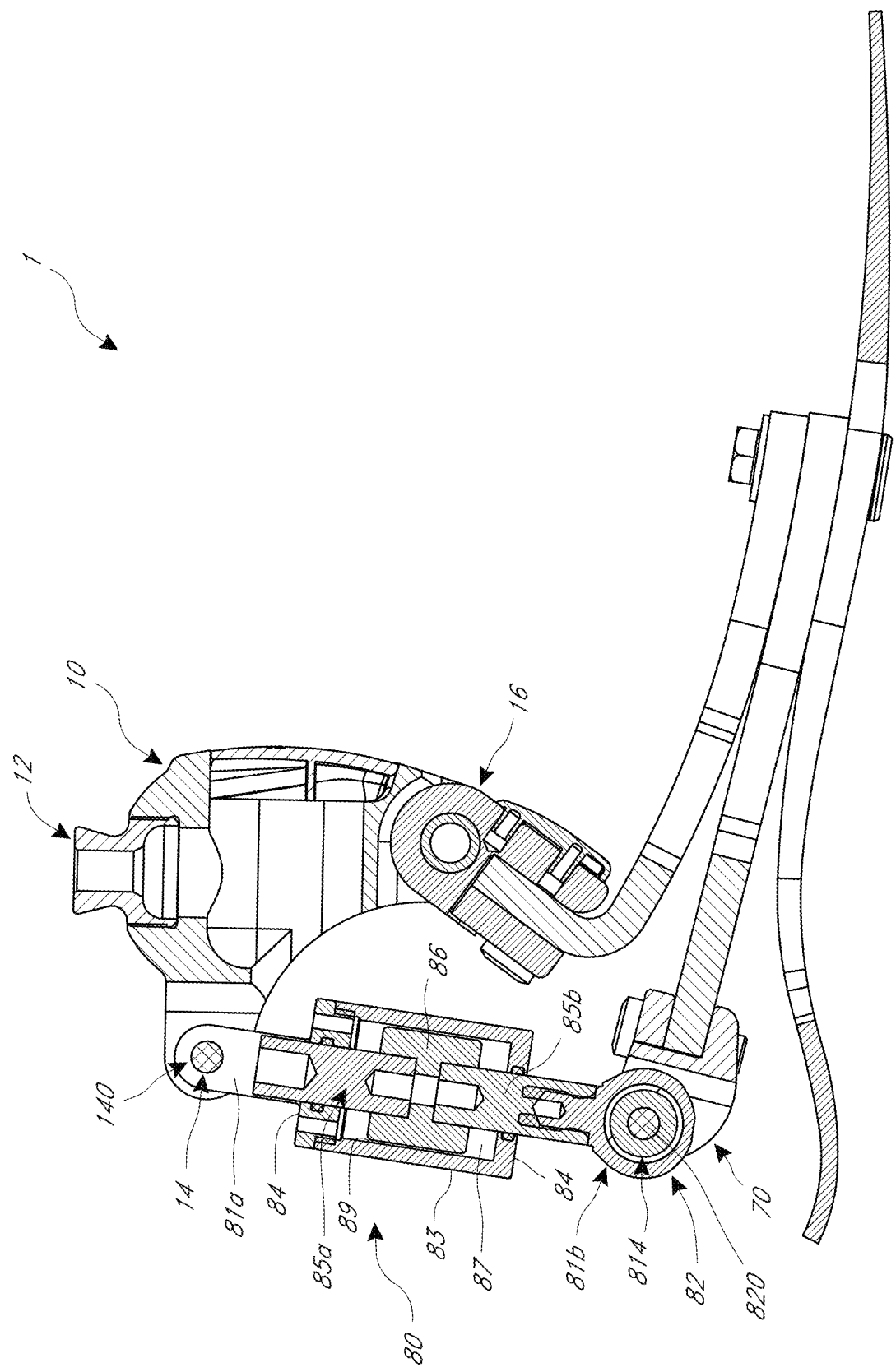
FIG. 1B is a cross-sectional view of the prosthetic foot of FIG. 1A.
Figure 1C:
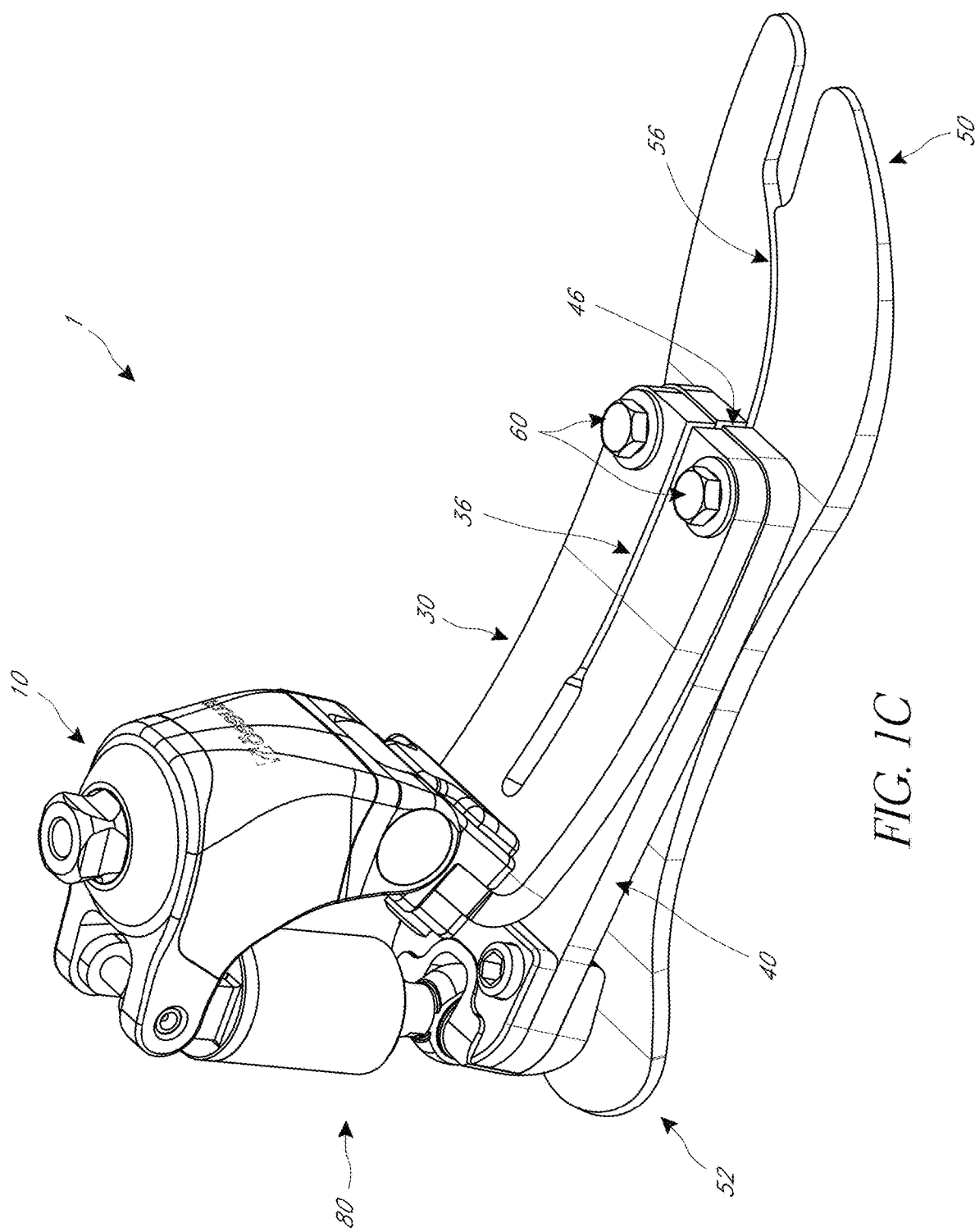
FIG. 1C is a perspective view of the prosthetic foot of FIG. 1A.
Figure 1D:
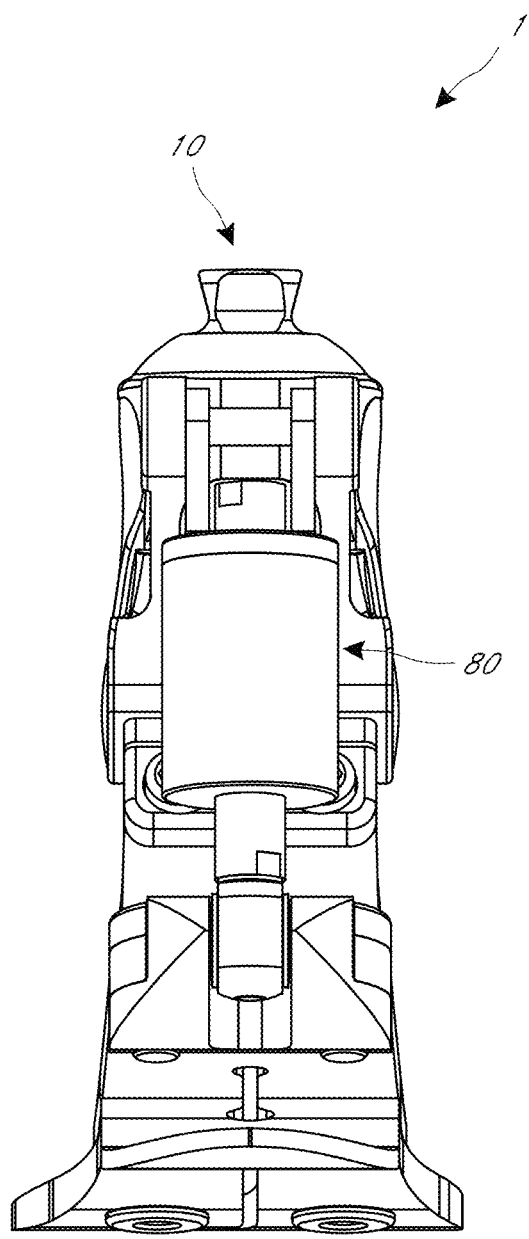
FIG. 1D is a rear view of the prosthetic foot of FIG. 1A.
Figure 1E:
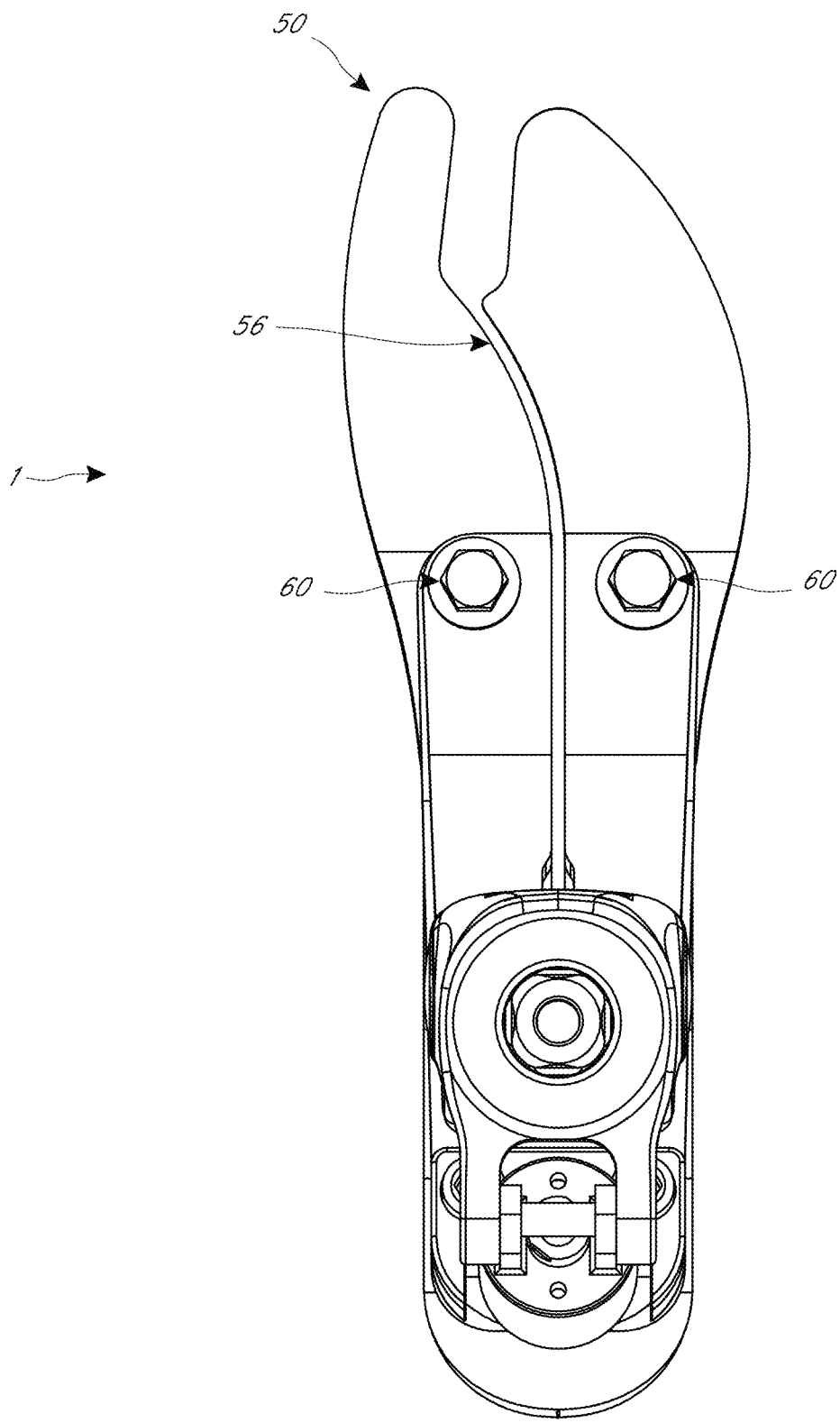
FIG. 1E is a top view of the prosthetic foot of FIG. 1A.
Figure 1F:
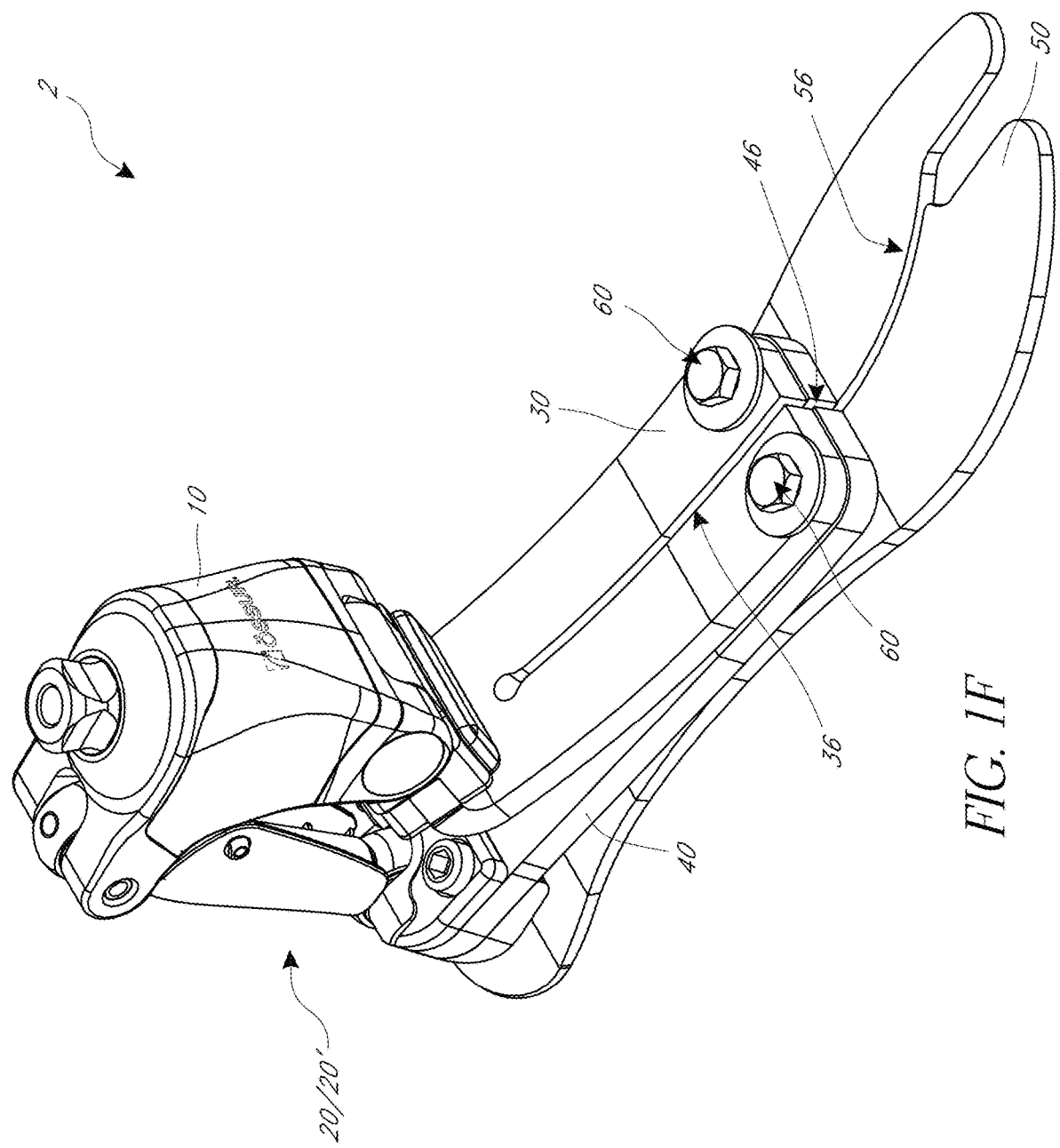
FIG. 1F is a perspective view of another embodiment of a prosthetic foot having a variable stiffness mechanism.
Figure 1G:
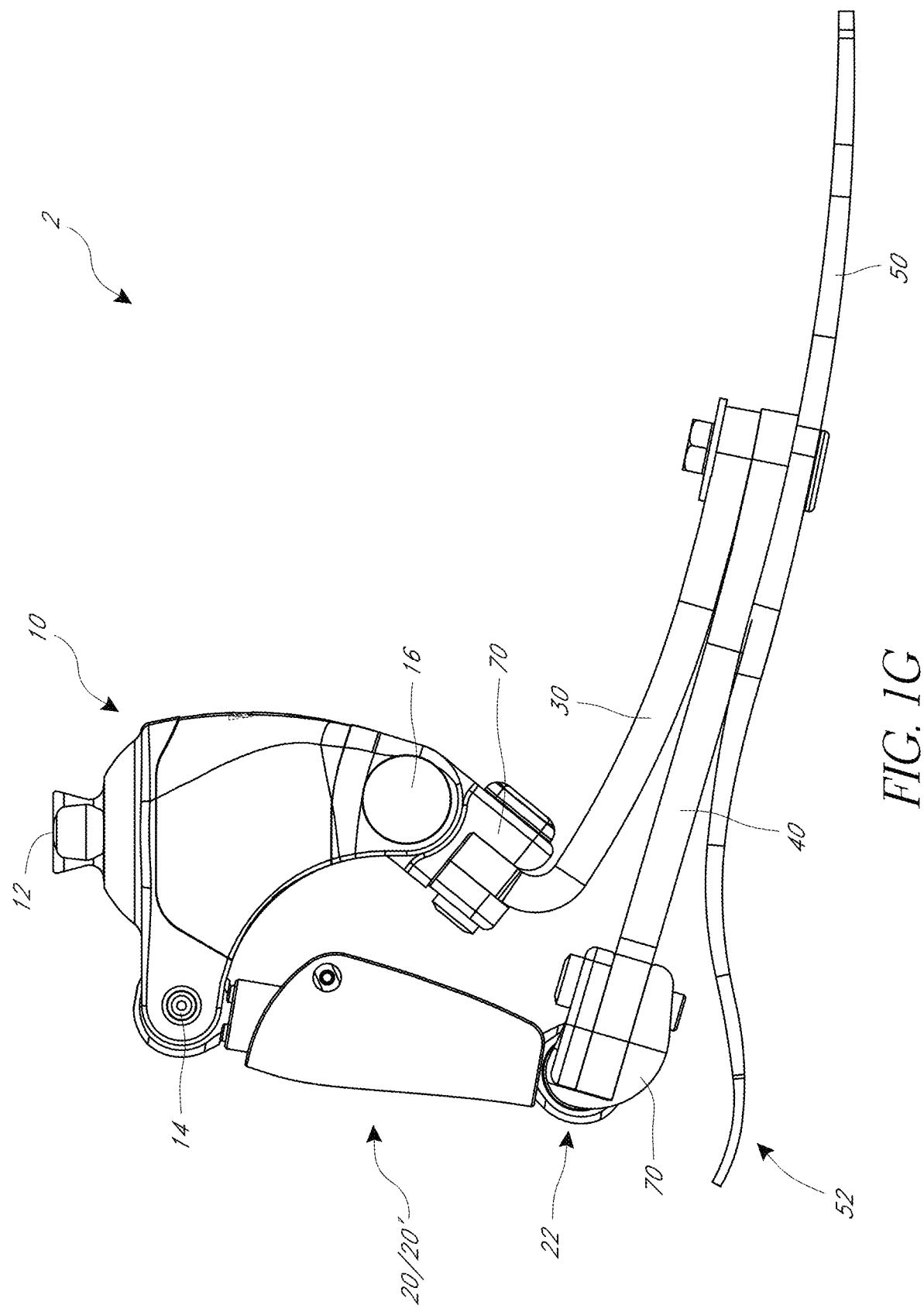
FIG. 1G is a side view of the prosthetic foot of FIG. 1F.

FIGS. 1A-1E illustrate an embodiment of a prosthetic foot 1. FIGS. 1F and 1G depict another embodiment of a prosthetic foot 2. The prosthetic foot 1 and prosthetic foot 2 can have substantially the same features except as described below.

The prosthetic foot 1 and the prosthetic foot 2 can attach to a user or to another prosthetic device with an attachment member 10. The attachment member 10 is depicted as including a first connection portion 12 shown as a pyramid connector. The pyramid connector can attach to a stump on a user, to another prosthetic device (e.g., a pylon, a socket), or to any other appropriate object. Further, it will be understood that the first connection portion 12 can include attachment features other than a pyramid connector, such as a threaded hole or screw, a latch, a magnetic member, tube clamp, or other features.

The attachment member 10 can additionally include second and third connection portions 14, 16. The attachment member 10 can serve to provide a rigid connection between the connection portions 12, 14, 16. For example, the attachment member 10 can include a substantially rigid material such as aluminum, steel, titanium, other metals or metallic alloys, carbon fiber, composites, or substantially rigid plastics. However, in other embodiments the attachment member 10 can provide flexibility, potentially in multiple planes. Thus, in some embodiments the attachment member 10 can include a more flexible material or include flexible joints between separate components of the attachment member 10. For example, in some embodiments the attachment member 10 can have a flexible connection with the first connection portion 12, allowing for motion in the medial/lateral and/or anterior/posterior directions. Further, the connection may allow torsional flexibility with the first connection portion 12. In other embodiments, as further described below, the attachment member 10 can have a flexible connection with one or both of the second and third connection portions 14, 16.

As shown in FIGS. 1A-1G, the attachment member 10 can connect to a first flexible member 30 (e.g., foot plate) at the third connection portion 16. In some embodiments, the third connection portion 16 can provide a rotatable connection (e.g., pivot joint), although non-rotatable connections can also be used. In some embodiments, the rotation can be provided by an axle firmly mounted to the attachment member 10, about which the first flexible member 30 can rotate. In other embodiments, the first flexible member 30 can be fixed to the axle (e.g., via a bracket or brace attached to the flexible member 30), and relative rotation can be allowed between the axle and the attachment member 10. In one embodiment, the first flexible member 30 (or brace attached to the flexible member 30) can include or define a bushing or opening through which the axle extends. The first flexible member 30 can be formed from a sufficiently flexible material such as carbon fiber, though other suitable materials or combination of materials can be used (e.g., carbon and glass fibers). In other embodiments, the first flexible member 30 can be substantially inelastic, so as to provide a rigid connection. It will be understood that the other flexible members 40, 50 (e.g., foot plates), which are described further below, can be formed of similar materials and have similar connections as the first flexible member 30.

Further, the first flexible member 30 can optionally be formed into a shape that provides a desired flexibility or rigidity. As shown in FIGS. 1A-1C and 1F-1G, the flexible member 30 can optionally be substantially L-shaped. The flexible member 30 can also optionally have a sharp corner. In other embodiments, the flexible member 30 can have other shapes, such as have a proximal portion that is angled (e.g. extends at an acute angle in the fore-aft direction, or extends at an obtuse angle in the fore-aft direction) relative to a distal portion of the flexible member 30.

In the illustrated embodiments, a third flexible member 50 extends from a heel portion 52 (e.g., a cantilevered or free end) at a bottom and rear portion of the prosthetic foot 1 or 2 along an entire length of the prosthetic foot 1 or 2 (e.g., extend from heel-to-toe). As shown in FIGS. 1C, 1F, and 1G, the third flexible member 50 can optionally include a slit 56 that extends longitudinally along the third flexible member 50 to separate the third flexible member 50 into two or more foot members that can flex at least partially independently. The slit 56 can be curved inward, and expand a toe region to define a "big toe" or hallux portion. Further, the third flexible member 50 can optionally curve inward and generally widen as it extends toward the toe portion such that the forefoot region is wider than the heel region. Further description is provided in U.S. Patent Publication No. 2015/0374514, which incorporated by reference herein in its entirety. In other embodiments, the third flexible member 50 may not include any slits.

A second flexible member 40 can be disposed above the third flexible member 50 and below the first flexible member 30. With reference to FIGS. 1F-1G, the second flexible member 40 can optionally extend from a proximal end operably coupled to a link 20, described in greater detail herein, to a distal end at a location that is proximal of the toe end of the third flexible member 50. In the illustrated embodiments, the second flexible member 40 optionally includes a slit 46 aligned with the slit 56 of the third flexible member 50. In other embodiments, the second flexible member 40 may not include any slits.

The first flexible member 30 can extend from a proximal end coupled to a bottom end of the attachment member 10 (e.g., via a bracket or brace attached to the proximal end of the first flexible member 30) to a distal end. In some embodiments, the distal end of the first flexible member 30 can be aligned or substantially aligned with the distal end of the flexible member 40. In other embodiments, the distal end of the first flexible member 30 can terminate proximal or distal to the distal end of the flexible member 40. In the illustrated embodiments, the first flexible member 30 optionally includes a slit 36 aligned with the slit(s) 46, 56 of the second 40 and/or third 50 flexible members. In other embodiments, the first flexible member 30 may not include any slits.

The first 30, second 40, and third 50 flexible members can be coupled to each other. For example, in the illustrated embodiments, fasteners 60, such as bolts, extend through and couple the flexible members 30, 40, 50. The fasteners 60 can be located at a location at or proximate the distal ends of the first 30 and second 40 flexible members. The fasteners 60 can be located proximal to the distal or toe end of the third flexible member 50. In one embodiment, the third flexible member can be excluded, so that the prosthetic foot 1 or 2 is defined by the first and second flexible members coupled to the attachment member or adapter 10, via a link 20 interconnecting the second flexible member and the attachment member 10 and one or more rotatable connections 14, 16, 22.

Other configurations and arrangements for the flexible members 30, 40, 50 are also possible. For example, the first 30 and/or second 40 flexible members can extend to the distal or toe end of the prosthetic foot. One of the first 30 and second 40 flexible members can be longer than the other (in other words, may extend to a distal end that is distal to the distal end of the other). The third flexible member 50 may extend from a heel end of the prosthetic foot to a distal end at a location that is proximal of the toe end of the prosthetic foot. The first flexible member 30 or a portion of the first flexible member 30 can optionally be C-shaped.

The prosthetic foot 1 includes an actuator 80 extending between and connecting the second flexible member 40 and the attachment member 10. As shown in FIGS. 1A and 1B, the actuator 80 has a first connector 81*a* that connects to the attachment member 10 at the second connection portion 14 of the attachment member 10. Like the second and third connection portions 14, 16, the fourth connection portion 82 can be rotatable or non-rotatable. In the illustrated embodiment, the first connector 81*a* includes two upwardly extending arms 810 (see FIG. 2A). Each arm 810 includes an opening 812 proximate a free end of the arm 810. A fastener 140 (e.g., a screw, bolt, axle, pin, or the like) can extend through the openings 812 and/or a bushing to couple the first connector 81a, and therefore the actuator 80, to the attachment member 10 at second connection portion 14. The actuator 80 can have a second connector 81b that connects to the second flexible member 40 at a fourth connection portion 82. In the illustrated embodiment, the connector 81b includes an opening 814 and/or a bushing. A fastener 820 (e.g., a screw, bolt, axle, pin, or the like) can extend through the opening 814 and/or the bushing to couple the connector 81b, and therefore the actuator 80, to the second flexible member 40 at the fourth connection portion 82. The second flexible member 40 can act as a spring leaf in series (such as being connected end-to-end) with the actuator 80. Although not shown in the illustrated embodiment, in some embodiments, the one or more springs parallel to the actuator 80 can be included in the foot 1 to provide a spring action to the movement of the actuator 80. The movement can be of the foot 1 relative to the proximal end of the second flexible member 40.

Figure 2A:
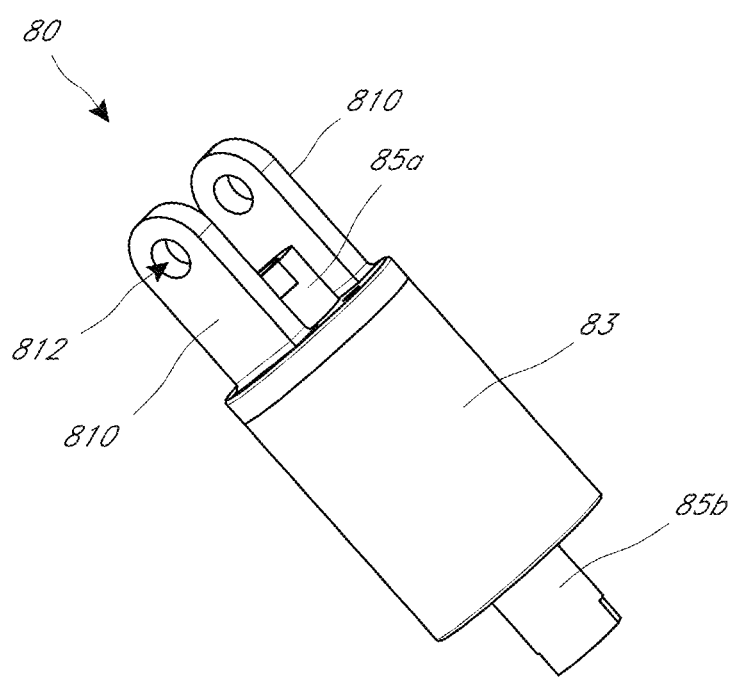
FIG. 2A is a perspective view of the STF actuator of the prosthetic foot of FIG. 1A.
Figure 2B:
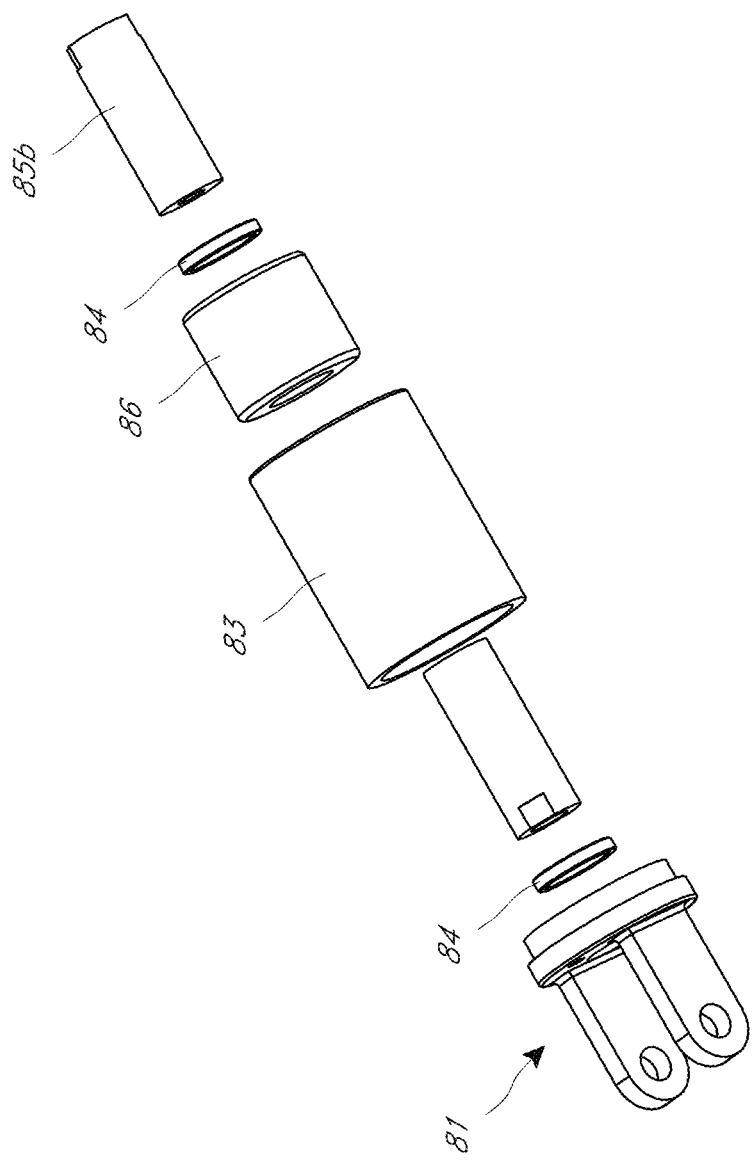
FIG. 2B is an exploded view of the actuator of FIG. 2A.

As shown in FIGS. 1B and 2A-2B, the actuator 80 can have a piston damper design. The actuator 80 is designed to move with low force resistance at low speeds, providing a damping effect. At higher speeds of motion, the actuator 80 stiffens and transfers the force exerted through the actuator 80 to the serial connected spring leaf (that is, the second flexible member 40), thereby providing a stiffer response of the foot. Therefore, the actuator 80 in combination with the serially connected second flexible member 40 and the parallel connected springs, can act as a variable stiffness mechanism to provide variable stiffness to the foot during use (e.g., depending of the speed of motion exerted by the user). The actuator 80 can include a cylinder 83. The cylinder 83 can have a predetermined inner diameter. The cylinder 83 can be closed and sealed at both ends, for example, with covers 84. The covers 84 can have a sealed opening configured for slidably accommodating a piston rod 85. As shown in FIGS. 1B and 2B, the piston rod 85 can include a first rod 85a and a second rod 85b. In other embodiments, the piston rod 85 can include a single rod. The piston rod 85 can enter the cylinder 83 through the sealed openings of the covers 84. In some embodiments, the first connector 81a can be coupled to or integrally formed with an upper end of the piston rod 85 or first rod 85a. In some embodiments, the second connector 81b can be coupled to or integrally formed with a lower end of the piston rod 85 or second rod 85b.

A piston 86 inside the cylinder 83 can be fixed to the piston rod 85. The piston 86 can be cylindrical. The cylindrical piston 86 can be of an outer diameter that is smaller than the inner diameter of the cylinder 83. The piston 86 can be in a concentric position relative to the cylinder 83 so that a thin gap or orifice 89 is between the inner wall of the cylinder 83 and the outer wall of the piston 86. In some embodiments, the gap or orifice can have a size of about 0.05 mm to about 1.0 mm. The dimension of the gap or orifice can be varied to vary the speed or rate of movement of the actuator 80. For example, the geometry (diameter and sequentially the length) of the piston (or cylinder) may be changed by using piezoelectric material or Shape Memory Alloys in the piston (and/or cylinder), thereby varying the gap dimension. In some embodiments, active control acquired by a "piston" with a geometry of flow channels (slits) that can be mechanically closed/opened can be used to vary the speed or rate of movement of the actuator 80. Increasing the actual gap length by opening up more slots in the piston and not increase the actual gap width or an orifice may be more preferable. In such embodiments, the piston may not be cylindrical. In some implementations, the piston may have a more complex geometry to increase the cross-sectional area of the gap or orifice while reducing the gap dimension (for example, by having radial slits along the length of the piston). The slots can be manufactured into the piston or be opened by a vane in a longitudinal direction of the piston. Other types and/or geometries of the piston can also be used (for example, a rotational piston, or a piston including a counter-part to the piston for opening and/or closing gaps/slits on the piston to adjust the effect of the actuator).

Figure 2C:
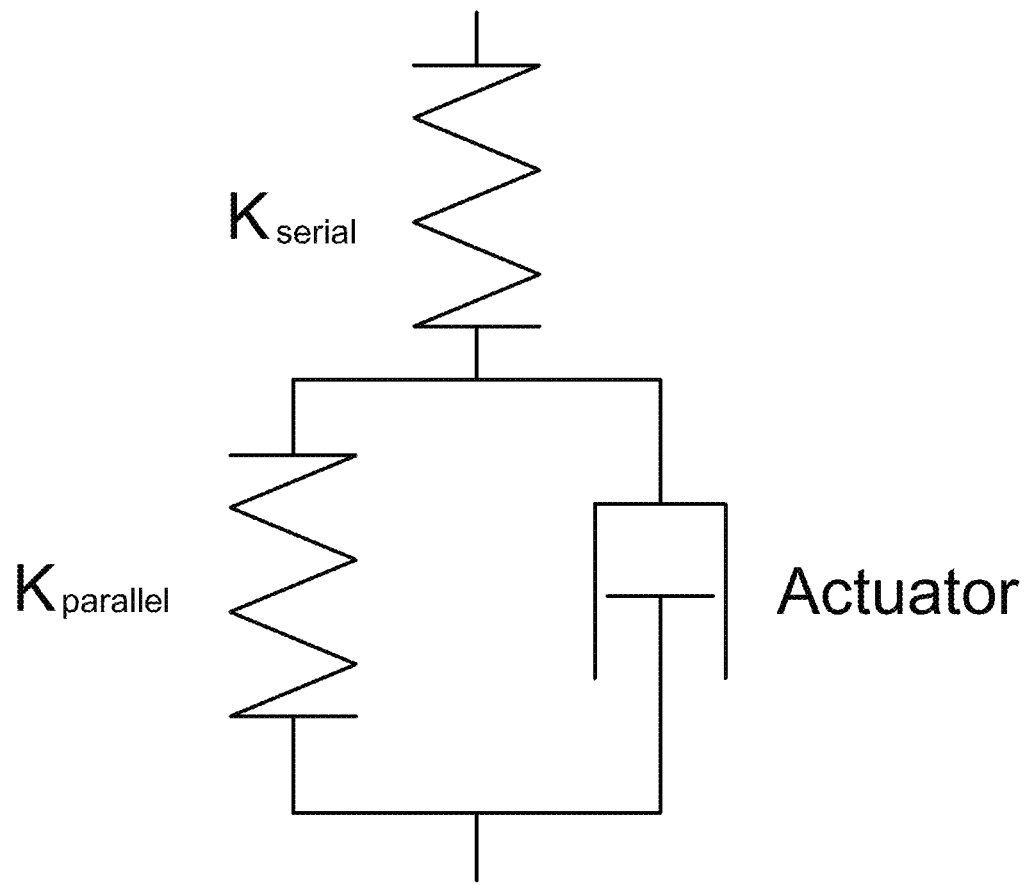
FIG. 2C is a schematic illustration of a variable stiffness mechanism.

In the variable stiffness mechanism disclosed herein such as shown in FIG. 2C, the spring constant of the parallel connected spring, Kp, is lower than the spring constant of the serial connected spring, Ks. At low velocities the softer spring (Kp) governs the stiffness. At higher movement rates, the actuator may over-dampen (such as severely over-dampen) the displacement over Kp and the stiffer spring (Ks) can govern the system stiffness. The parallel spring action to the movement can be translated to a more rigid response in movements at a velocity of normal and hurried walking but a softer response, with a greater range of motion, in slower movements, such as when the foot is being adjusted before the amputee stands up from a chair or executes other relaxed ambulation. The parallel spring can allow the system to revert back to the zero-position after deformation/flexion.

The cylinder 83 and the covers 84 define an internal compartment 87. During use, the piston 86 can move within the compartment 87. For example, flexing of the distal or toe portion of the prosthetic foot 1 (for example, during heel strike) can cause the piston 86 to move toward the fourth connection 82, and extending the distal or toe portion of the prosthetic foot (for example, during toe off) can cause the piston 86 to move toward the second connection portion 14. The compartment 87 can be filled with a fluid that is pushed through the orifice between the piston 86 and cylinder 83 as the piston 86 moves. The movement of the fluid can be in an opposite direction to the movement of the piston 86. For example, when the piston 86 is moving toward the fourth connection portion 82, the fluid can flow toward the second connection portion 14. Conversely, when the piston 86 is moving toward the second connection portion 14, the fluid can flow toward the fourth connection portion 82.

The fluid in the compartment 87 can have complex viscosity properties (for example, being non-Newtonian) so that the fluid can exhibit a shear thickening effect. In some embodiments, the fluid in the compartment 87 is a Shear Thickening Fluid. Shear Thickening Fluids (STF) are fluids that react to the rate at which shear stresses are applied such that the higher the shear rate, the higher is the apparent viscosity of the fluid. In some embodiments, the STF can include a hydrophilic shear thickening fluid formulation. The formulation can be non-toxic and/or non-volatile. The fluid can aid in absorbing impact energy. In some embodiments, the STF can exhibit higher shear thickening at rates relevant to human motion, such as walking, moving around, or otherwise.

Figure 3:
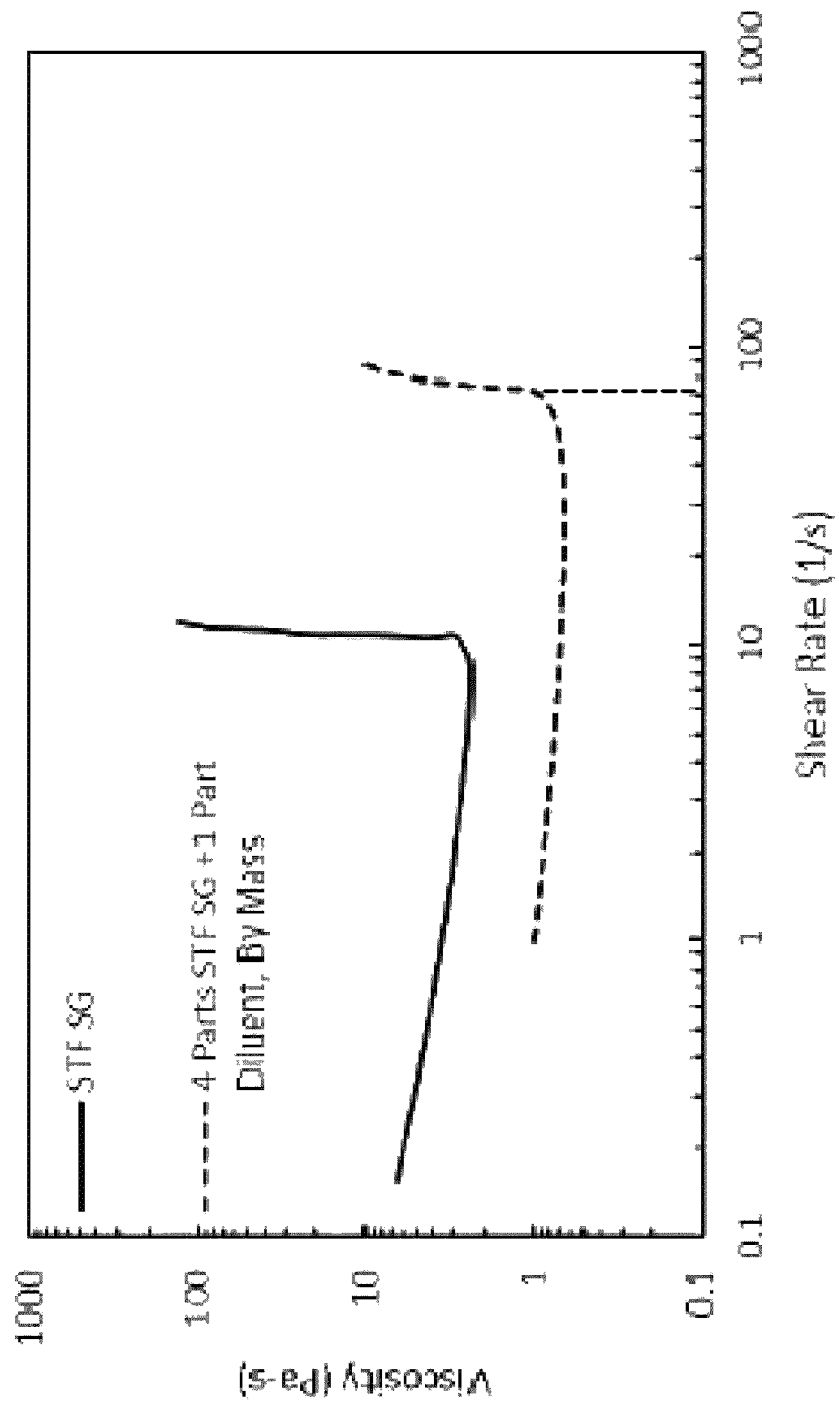
FIG. 3 shows a graph of a viscosity of a hydrophilic shear thickening fluid at various shear rates.

Some STFs exhibit a Discontinuous Shear Thickening (DST) effect. The DST effect is exhibited in fluids that show a discontinuous jump in apparent viscosity when a critical point in shear rate is reached. STFs exhibiting the DST effect can include a densely packed suspension of solid particles on the micro and/or nano scales in a viscous fluid. The DST effect originates from dilatant behavior that results in particle jamming under critical conditions. In certain regions, the apparent viscosity of the fluid can show a shear thinning effect before and after the critical shear rate. FIG. 3 illustrates example viscosities (for example, at room temperature of about 25° C.) of an STF and an STF mixed with an optional diluent (such as the STF SG shear thickening fluids from STF Technologies LLC). The undiluted STF exhibits a critical shear rate of about 10 s$^{-1}$. The diluted STF exhibits a critical shear rate of about 80 s$^{-1}$. Accordingly, use of the optional diluent can facilitate optimizing the critical shear rate. The actuator 80 can be adjusted so that the STF in the compartment 87 is in the high viscosity regime above the critical shear rate as movements are rapid, but more compliant when the movement is slower.

As shown in FIG. 1B, the piston rod 85 is through-going as the piston rod 85 extends through the piston 86 and both covers 84. The through-going piston rod 85 can eliminate a need for a compensator to account for the volume change of the fluid-filled space between the cylinder 83 and the piston 86/rod 85 assembly when the piston 86 is moved relative to the cylinder 83. In other embodiments, the actuator 80 can have a piston 86/rod 85 assembly or rod 85 that only extends through one cover 84 and partially through the cylinder 83. Additional measures can be taken to account for the change of volume as the piston 86/rod 85 is pushed into and out of the cylinder 83. For example, the additional measures can include an accumulator such as a pressurized bladder, a floating piston, or other suitable mechanisms.

In the embodiment illustrated in FIGS. 1F and 1G, instead of an STF actuator, the prosthetic foot 2 includes a link 20 extending between and connecting the second flexible member 40 and the attachment member 10. As shown, the link 20 connects to the attachment member 10 at second connection portion 14. The link 20 connects to the second flexible member 40 at a fourth connection portion 22. Like the second and third connection portions 14, 16, the fourth connection portion 22 can be rotatable or non-rotatable.

In some embodiments, the link 20 is a rigid mechanical link. In use, the link 20 bends or moves the second flexible member 40 into either compression or extension as the user walks. The rigid link 20 and pivot joint 16 allow for a higher range of motion about the pivot joint 16 with a medium stiffness, which allows the prosthetic foot 2 to be better adapted for normal walking. The link 20 influences the rotation of the prosthetic foot 2 about the pivot joint 16 in use and interacts with the second flexible member 40.

In some embodiments, instead of a rigid mechanical link, the link 20 is or includes a variable stiffness link. The variable stiffness link 20 can advantageously change its mechanical behavior. For example, the stiffness of the link 20 can be changed based on parameters such as the user's gait speed or impact force during heel strike. The variable stiffness link 20 can be non-powered, including for example, a speed dependent material (which can be a non-Newtonian fluid or share thickening fluid damper described above with reference to FIGS. 1A-1E and 2A-2B), a fluid damper, a damper in combination with a spring, and/or series elastic spring elements, or can include, for example, a magnetorheological brake, a magnetorheological damper, an electrorheologic damper, an electro-active damper, electro-active polymer(s), an electroadhesive brake, and/or piezoelectric material(s) (such as piezo-electric polymer foams), electrets. A speed dependent material (or another variable stiffness mechanism, such as described herein) can vary in compression and/or extension to adapt to various gait speeds, phases of the gait cycle, and/or activities. The speed dependent material or other variable stiffness mechanism can vary or act in compression and extension independently, with different characteristics in compression than in extension. A fluid damper can passively allow for variable stiffness and/or speed dependent characteristics due to, for example, a self-adjustable valve. A damper can advantageously allow for a smoother transition during roll over during the user's gait cycle and/or a damped impact. A magnetorheologic (MR) damper can allow for adjustable damping values via microprocessor control to control the application of an electric or magnetic field to the MR damper to vary its stiffness. However, a variable stiffness link 20 that includes an active mechanism and/or microprocessor control may be heavier and require a power source.

The properties of a speed dependent material can advantageously vary with or adapt to different gait speeds of the user in use. Such different gait speeds can result in different rates of compression of the material, and the material can exhibit different stiffness properties based on the different rates of compression. The material can be, for example, a non-Newtonian material, an open or closed cell polyurethane foam, a shear thickening material or fluid, or another suitable polymer. An example of a material that can be used is a material sold by D3O.

Figure 4:
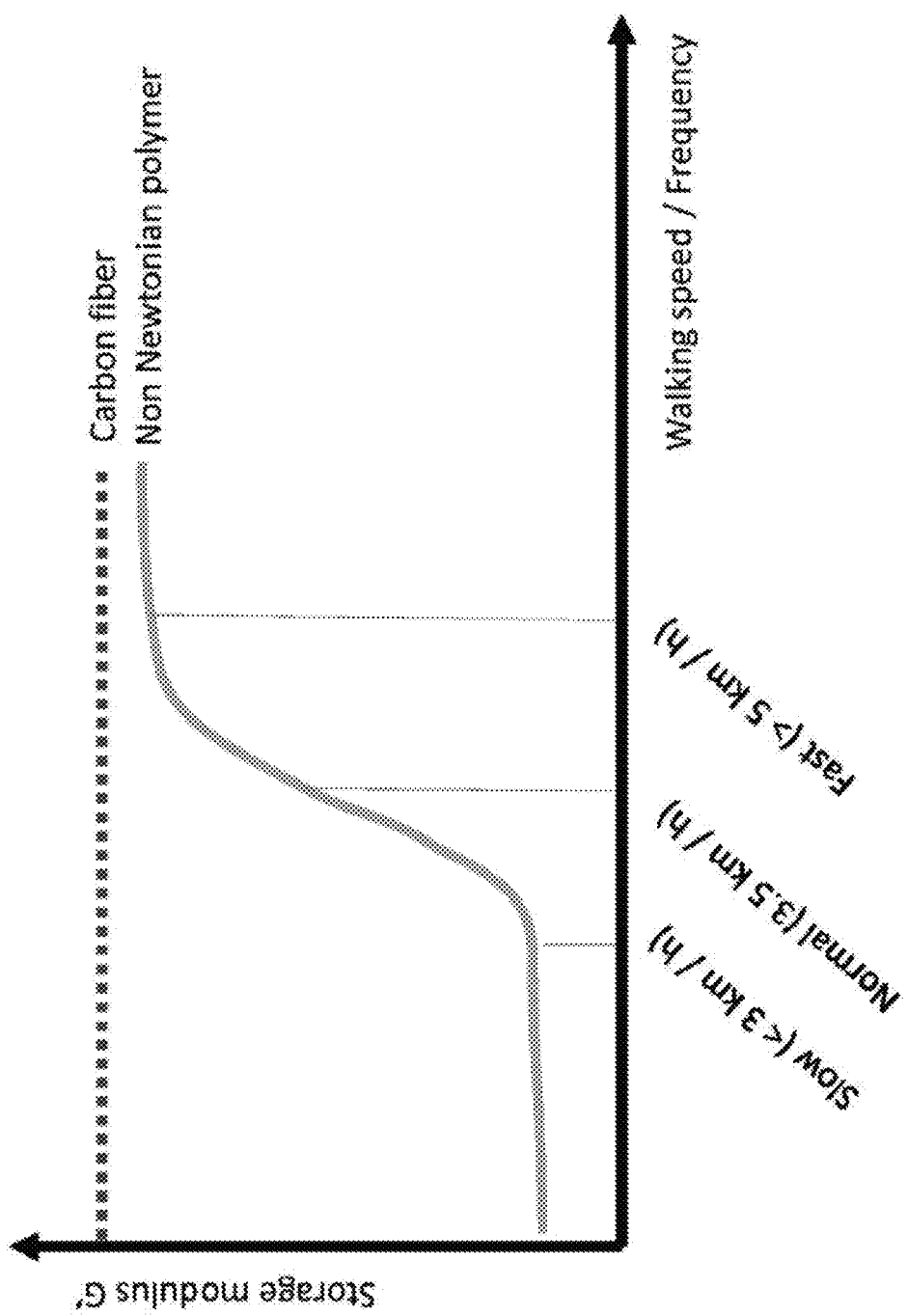
FIG. 4 is a graph of storage modulus G' vs. walking speed for a material having variable stiffness properties.

The material compresses relatively faster at relatively higher walking speeds (e.g., greater than about 3 km/h) and relatively slower at relatively slower walking speeds (e.g., slower than about 3 km/h). The material selected preferably exhibits a relationship of storage modulus G' relative to temperature and/or frequency of impact (i.e., walking speed) as shown in the graph of FIG. 4. As also shown in FIG. 4, the storage modulus G' of carbon fiber remains the same, or substantially the same regardless of walking speed. As shown, the speed-dependent material, when subject to ambient environmental temperature, exhibits a steep gradient change as walking speed increases from slow, e.g., less than about 3 km/h, to fast, e.g., greater than about 5 km/h. The material can exhibit soft foam-like behavior with higher damping and lower rebound at slow walking speeds, and harder, less damping, with higher rebound behavior at fast walking speeds. The steep gradient change or steep slope of the graph indicates that the material provides a significant change in stiffness when transitioning from slow to fast speeds (and vice versa). As the impact frequency increases, the material can harden and exhibit shear thickening (that is, the viscosity of the material, such as a fluid, increases with the rate of shear strain). The shear thickening can provide non-linear impact speed-dependent material properties.

Figure 5:
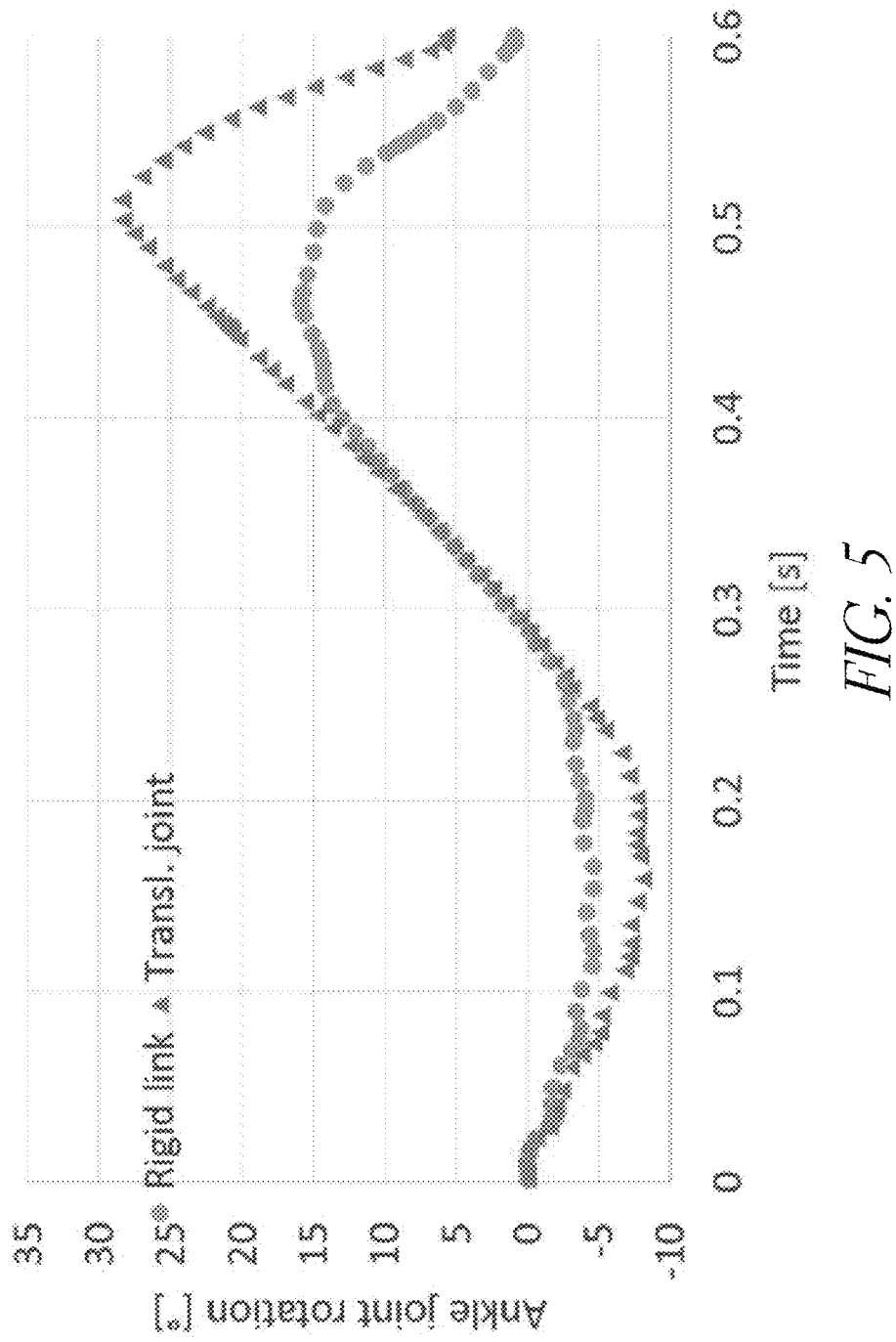
FIG. 5 shows a graph of ankle joint rotation vs. time for a prosthetic foot including a variable stiffness element.

The material can advantageously allow the prosthetic foot 1 to provide relatively high damping and energy absorption with a larger range of motion when the user is walking at relatively slow walking speeds, and high energy return, low damping when the user is walking at relatively faster walking speed. FIG. 5 shows a graph of ankle joint rotation (e.g., rotation about connection portion 16) vs. time for the prosthetic foot of FIGS. 1F and 1G including the rigid mechanical link 20 compared to the prosthetic foot of FIGS. 1F and 1G including a variable stiffness link 20' such as a translational link or a link including a spring and damper element or when the variable stiffness link 20' is an STF actuator like the STF actuator 80 shown in FIGS. 1A-1E. As shown, the variable stiffness link 20' can provide a greater range of ankle joint rotation than the rigid stiffness link 20.

By varying the stiffness of the STF actuator 80 or the variable stiffness link 20', the prosthetic foot 1 or 2 can advantageously adapt (e.g., automatically adapt) to various gait speeds, phases of the gait cycle, and/or activities. For example, at low or slow walking speeds, the STF actuator 80 or the variable stiffness link 20' can have lower damping and lower stiffness, which can reduce the spring force from or at connection portion 82 or 22 and allow a greater range of motion about the pivot joint 16. At higher or faster walking speeds, the damping can increase, which can increase the stiffness, e.g., increase the use of spring force from or at connection portion 82 or 22, and reduce the range of motion about the pivot joint 16. This can advantageously lead to better energy return of the overall prosthetic foot 1 or 2. Moreover, such variable stiffness operation of the actuator 80 advantageously occurs without the use of electronics (e.g., processors, sensors, batteries, etc.) which can add weight and complexity to the prosthetic foot.

In the prosthetic foot 1 or 2, the second flexible member 40 can be coupled to the link 20 or the actuator 80 via a brace 70. The brace 70 can mount around (e.g., over) the proximal end of the second flexible member 40. A hole in the brace 70 can facilitate connection to the link 20 or the actuator 80 with an axle. The brace 70 can have a C-shape with an opening that receives the second flexible member 40 as shown in FIGS. 1A and 1G. The brace 70 can be secured to the second flexible member 40 after it has been made, for example with screws or other fasteners. In other embodiments, the brace 70 can be coupled to the second flexible member 40 via other suitable mechanisms (e.g., an adhesive, press-fit connection). Alternatively, the second flexible member 40 can include or define a bushing or opening through which an axle extends to provide a rotatable connection or pivot axis between the second flexible member 40 and the link 20 or the actuator 80.

The first flexible member 30 can attach to the attachment member 10 at the third connection portion 16 with a similar brace 70. The braces 70 can be substantially similar in their attachment to the flexible members 30, 40. The braces 70 can be rotatably or non-rotatably (or pivotably or non-pivotably) coupled to the link 20 (or the actuator 80) and/or attachment member 10 at connection portions 22 (or 82), 16.

In some embodiments, connection portion 16 forms a pivot joint. In other words, the first flexible member 30, or the brace 70 coupled to the first flexible member 30, is pivotably coupled to the attachment member 10 at connection portion 16.

Figure 6A:
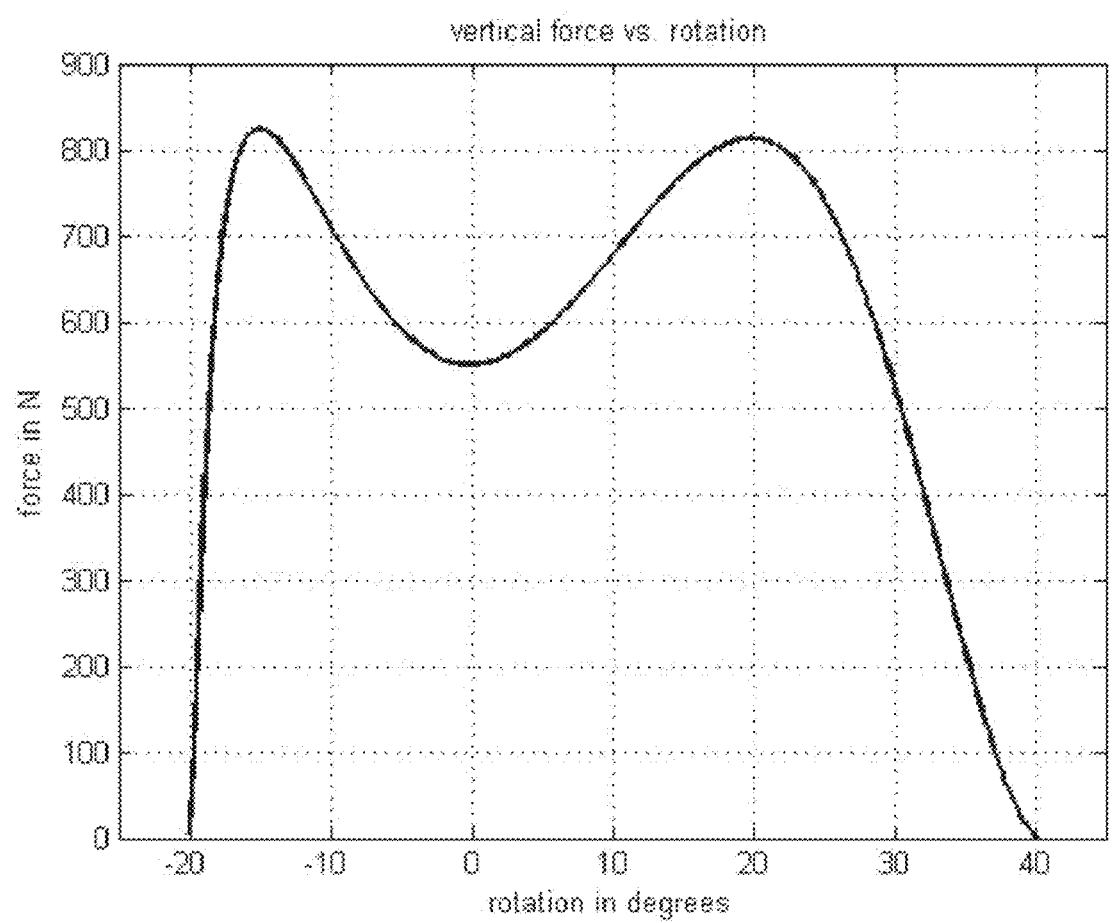
FIG. 6A shows input data for testing of a prosthetic foot.
Figure 7A:
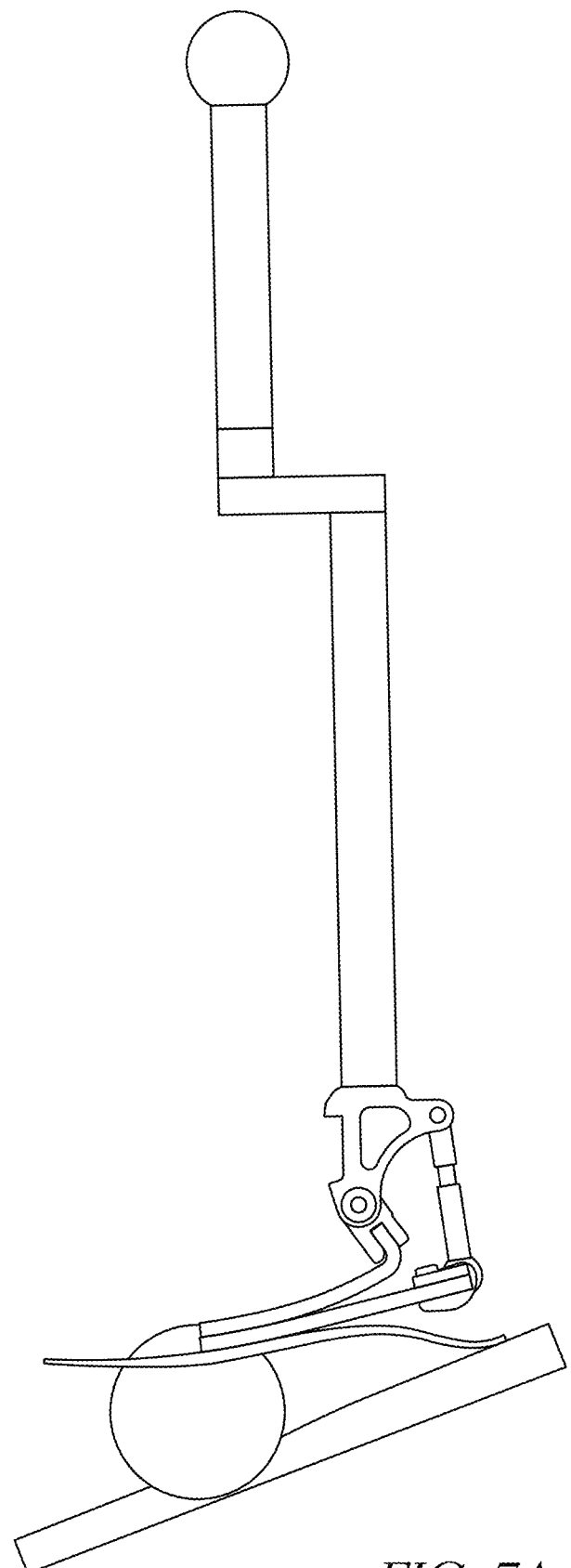
FIG. 7A shows a finite element simulation model of the prosthetic foot at early heel strike.
Figure 7B:
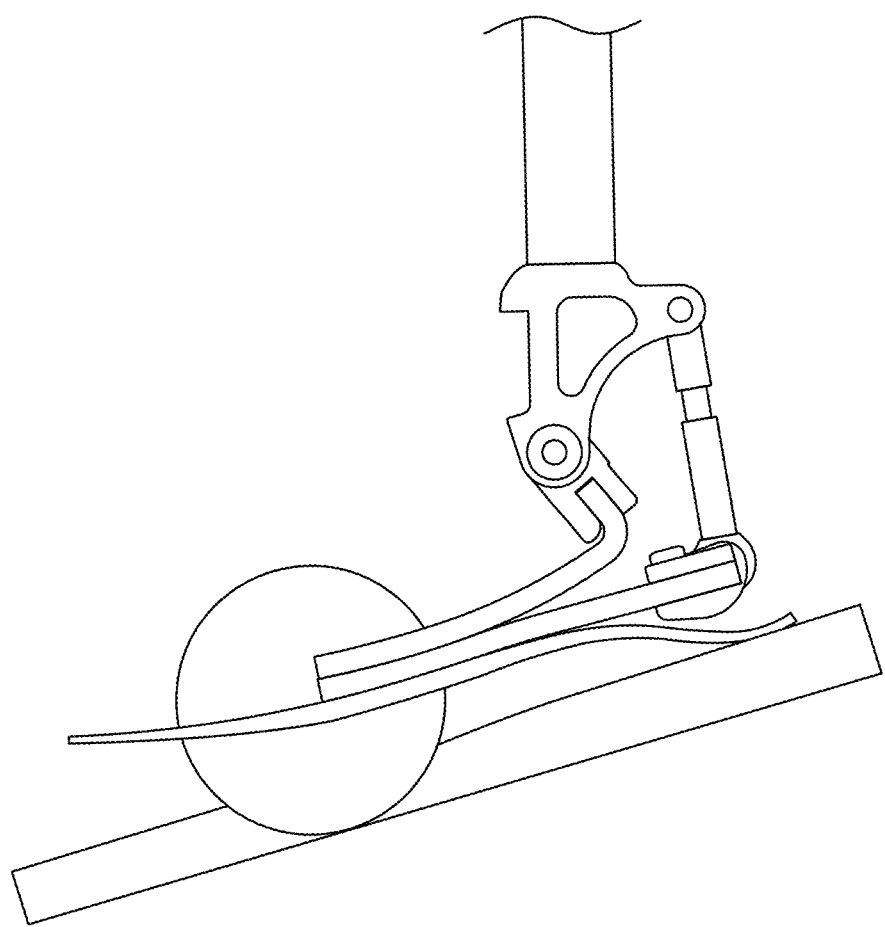
FIG. 7B shows the model of FIG. 7A at mid heel strike and maximum vertical force.
Figure 7C:
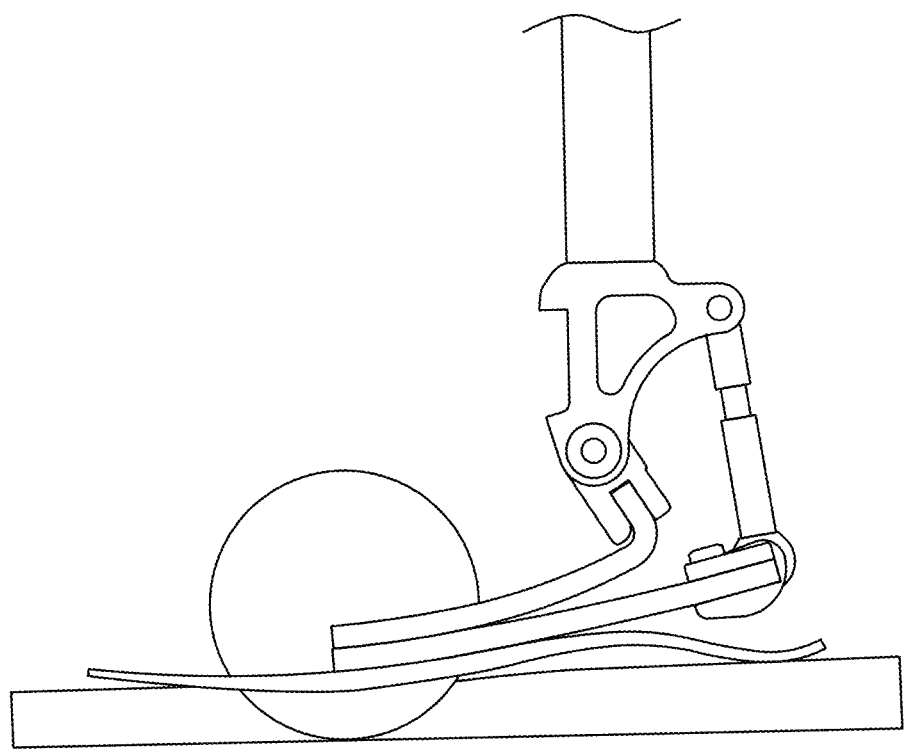
FIG. 7C shows the model of FIG. 7A a mid-stance.
Figure 7D:
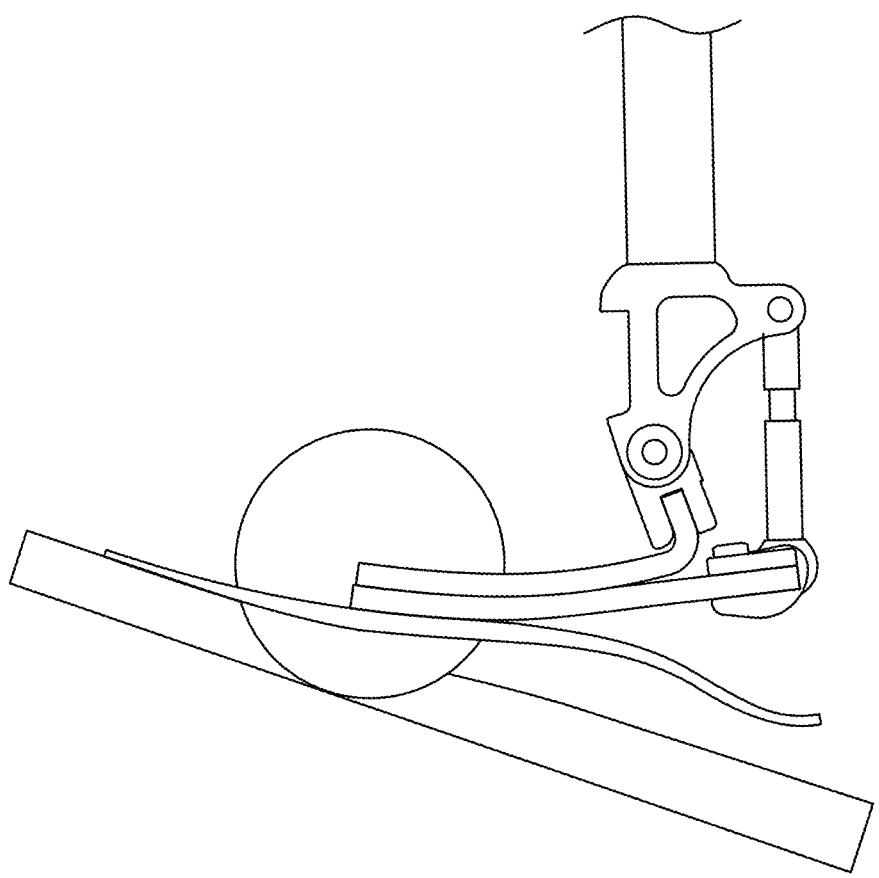
FIG. 7D shows the model of FIG. 7A following heel-off.
Figure 7E:
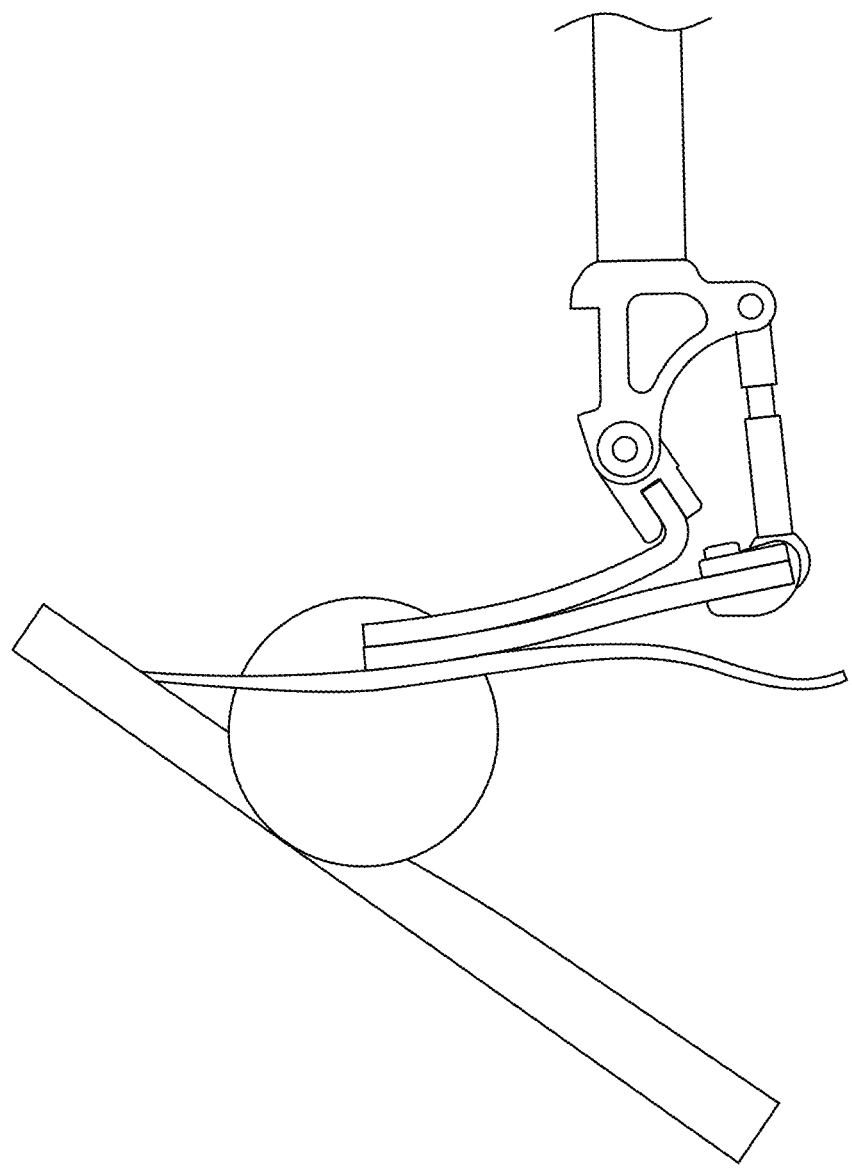
FIG. 7E shows the model of FIG. 7A before toe-off.
Figure 8A:
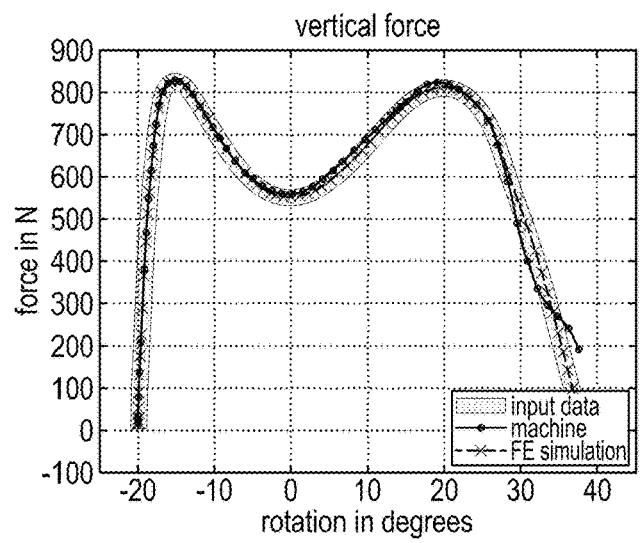
FIGS. 8A-8C show results of the mechanical testing.
Figure 8B:
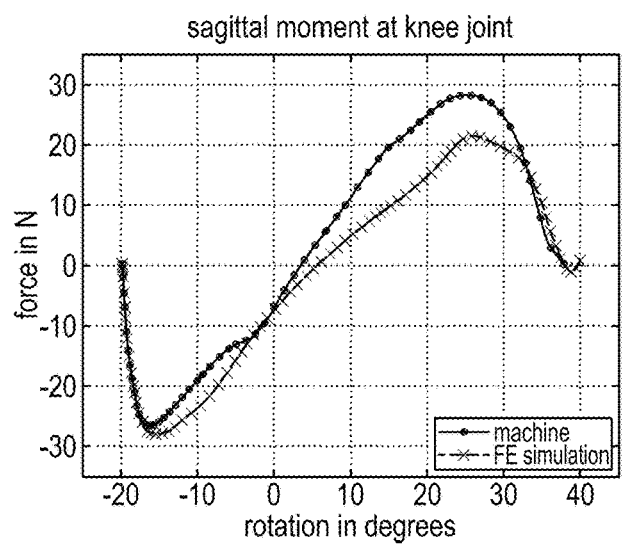
Figure 8C:
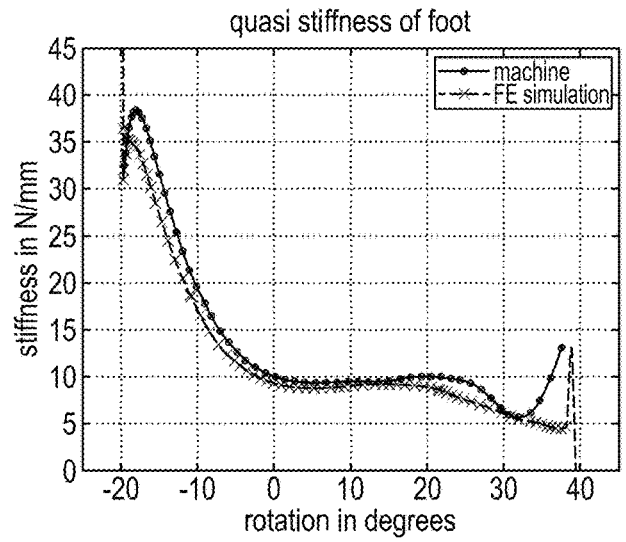

FIGS. 8A-8C illustrate results of testing the prosthetic foot of FIGS. 1F and 1G including the rigid mechanical link 20. The quasi-stiffness shown in the graph of FIG. 8C was calculated as the vertical force divided by the vertical displacement. The testing involved a heel-to-toe roll-over test according to ISO 16955 (e.g., by applying a dynamic force of 824N maximum, synchronized to a rotational motion ranging from a −20° to +40° angle during 0.6 second of stance phase) as shown in FIGS. 6A and 6B. For testing, the prosthetic foot 400 (which can be the prosthetic foot 2 described herein) was suspended via a ball joint 402, as shown in FIG. 6B. A bottom surface of the foot 400 can be 700 mm below the ball joint 402. A linear piston 406 can apply a low spring force (e.g., about 14N) to the foot 400 via the ball joint 402. A load cell (such as a 6 degree-of-freedom load cell) 408 can be coupled to the ball joint 402 (e.g., 200 mm below the ball joint 402). A linear shift bar 410 can be coupled an ankle of the foot 400 to the load cell 408 at a location offset from the load cell 408 so that the force is applied through a center of mass of the foot 400. The foot 400 was also coupled to a title table 404. The tilt table 404 can provide the desired rotational range of motion (e.g., at least −20° to +40° angle). The ball joint 402 can reset the foot during swing phase so that the foot was capable of rolling and deforming feely under the set load profile.

Finite element simulation testing was also performed to validate the testing, as illustrated in FIGS. 7A-7E. In the finite element model, the foot members are modeled as flexible surface bodies. Other parts of the foot are simplified to four rigid bodies in the model, that is, main body (Pyramid adapter), mechanical link, and two blade clamps. The three joints between the rigidly modeled bodies have a rotational degree of freedom about an axis, at each connection of the mechanical link and at the pivot connection of the top blade to the main body. Simulation was done to validate the finite element model against the ISO 16955 test procedure. The tilt table and linear shift geometry was modeled as rigid bodies and a transient structural analysis performed with test machine input data as boundary conditions for the simulation as shown in FIGS. 7A-7E. Values from the simulation were compared to the mechanical test output data, that is, the vertical displacement of the ball joint, the force reaction and the moment at knee level as show in FIG. 6B. The mechanical test according to ISO 16955 and the finite element module simulation showed comparable results during a full roll-over of the prosthetic sample, as shown in FIGS. 8A-8C.

Figure 9A:
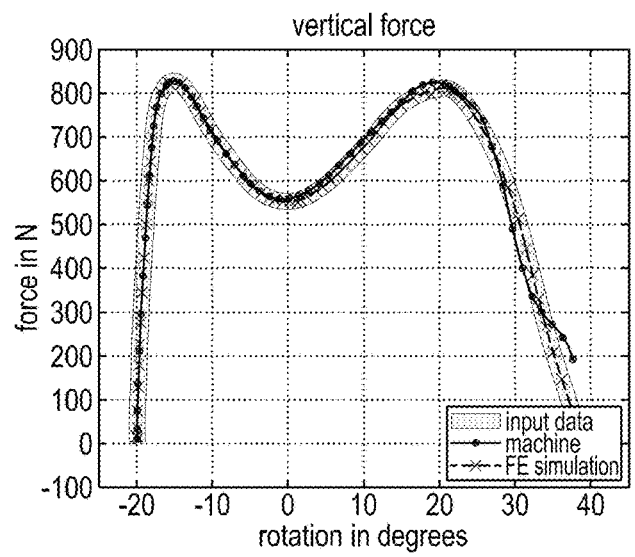
FIGS. 9A-9C show results of testing another embodiment of a prosthetic foot.
Figure 9B:
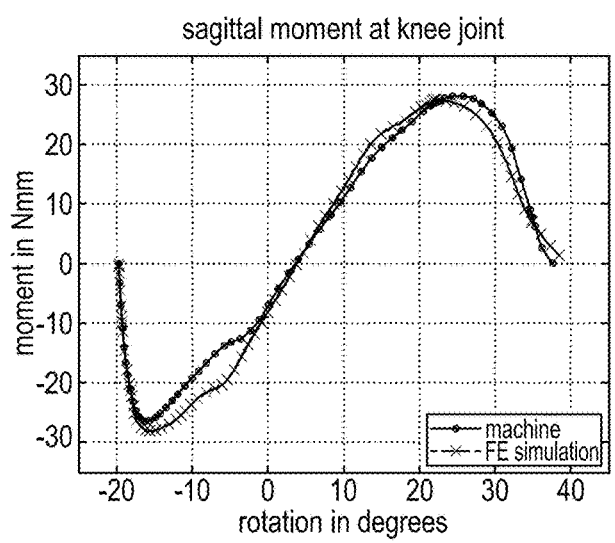
Figure 9C:
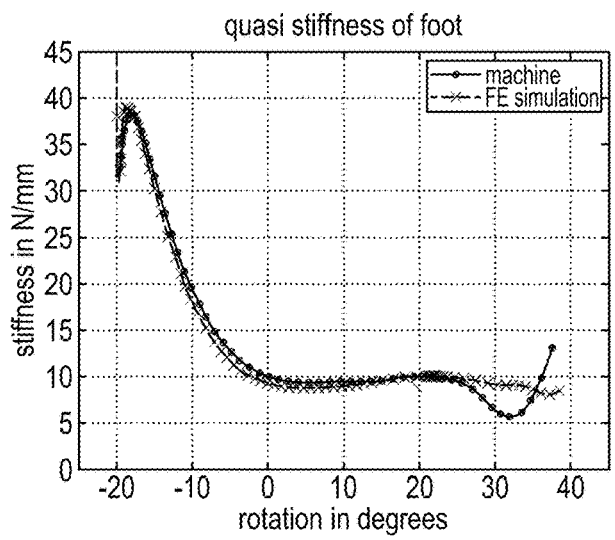

FIGS. 9A-9C illustrates results of testing the prosthetic foot of FIGS. 1F and 1G with a link 20' including a spring and damper element. The initial parameters for spring stiffness and dampening for the link 20' were set at a relatively high spring constant and low damping coefficient (k=200 kN/m; c=10 kN s/m). The results indicate that the prosthetic foot with the link 20' including the spring and damper element does not change stiffness as evenly as it would using only softer carbon fiber spring blades (e.g., without the spring and damper element link 20'. The spring and damper element link 20' therefore alters the overall transition and mechanical behavior of the foot, which may be advantageous during stair ambulation, when walking over slopes, or when walking at slow speeds. At higher speeds, it would be preferable to reduce the flexibility of the prosthetic foot.

Though the variable stiffness mechanism is described above in connection with a prosthetic foot design, the variable stiffness mechanism can be incorporated into other prosthetic or orthotic devices to improve the gait performance of the device. For example, the variable stiffness mechanism can be incorporated into an ankle-foot orthosis (AFO) that can be utilized to support a user that suffers from a drop foot condition, or a knee-ankle-foot orthosis (KAFO) that can be utilized to support a user that suffers from pain, weakness or instability in their leg.

Conditional language used herein, such as, among others, "can," "could," "might," "may," "e.g.," and from the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it may be understood that various omissions, substitutions, and changes in the form and details of the ground contact sensing system, including the sensor components, logical blocks, modules, and processes illustrated may be made without departing from the spirit of the disclosure. As may be recognized, certain embodiments of the systems described herein may be embodied within a form that does not provide all of the features and benefits set forth herein, as some features may be used or practiced separately from others. Additionally, features described in connection with one embodiment can be incorporated into another of the disclosed embodiments, even if not expressly discussed herein, and the prosthetic device having the combination of features still fall within the scope of the invention. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A lower limb support device comprising:
an attachment member configured to operably connect to a lower limb of a user;
a first flexible member extending from a proximal end to a distal end, the proximal end connected to the attachment member;
a second flexible member extending from a proximal end to a distal end; and
a link extending between and connecting the proximal end of the second flexible member and the attachment member, the link comprising a variable stiffness mechanism that is non-powered, wherein a stiffness of the variable stiffness mechanism varies based on a gait speed of the user, the variable stiffness mechanism comprising:
a cylinder having sealed openings on two ends of the cylinder along a longitudinal axis of the cylinder;
a piston assembly comprising a single-piece piston enclosed within the cylinder and defining a pair of chambers within the cylinder on opposite sides of the piston along the longitudinal axis of the cylinder, the piston comprising a solid material,
the piston assembly further comprising a piston rod having a first end and a second end extending from opposite sides of the piston and extending outside the cylinder via the sealed openings of the cylinder, the first end operably connected to the proximal end of the second flexible member and the second end operably connected to the attachment member, the piston assembly configured to translate along the longitudinal axis of the cylinder.

2. The lower limb support device of claim 1, wherein the lower limb support device is a prosthetic foot.

3. The lower limb support device of claim 1, wherein the attachment member comprises a pyramid connector.

4. The lower limb support device of claim 1, further comprising a third flexible member coupled to the first and second flexible members.

5. The lower limb support device of claim 1, wherein the proximal end of the first flexible member is rotatably connected to the attachment member.

6. The lower limb support device of claim 1, wherein the variable stiffness mechanism comprises a speed-dependent material.

7. The lower limb support device of claim 6, wherein the speed-dependent material is a non-Newtonian material.

8. The lower limb support device of claim 1, wherein the variable stiffness mechanism comprises a fluid damper, a damper and a spring, one or more elastic spring elements, or a shear thickening material or fluid.

9. The lower limb support device of claim 1, wherein the variable stiffness mechanism acts in one or both of compression and extension.

10. The lower limb support device of claim 9, wherein the variable stiffness mechanism acts in compression and extension independently with different characteristics.

11. A prosthetic foot comprising:
an attachment member comprising a connector configured to connect the attachment member to a user or another prosthetic device;
a first flexible member extending from a proximal end to a distal end, the proximal end connected to the attachment member;
a second flexible member extending from a proximal end to a distal end; and
an actuator extending between and connecting the proximal end of the second flexible member and the attachment member, the actuator being non-powered, the actuator comprising:
a cylinder having sealed openings on two ends of the cylinder;
a piston enclosed within the cylinder and defining a pair of chambers within the cylinder on opposite sides of the piston, the piston configured to translate along a longitudinal axis of the cylinder, the piston operably coupled to the proximal end of the second flexible member and the attachment member; and
a volume of shear thickening fluid disposed in one or both of the chambers within the cylinder, wherein an outer circumference of the piston is smaller than an inner wall of the cylinder such that the shear thickening fluid configured to pass from one chamber to the other chamber via an orifice defined by the outer circumference of the piston and the inner wall of the cylinder as the piston moves within the cylinder,
wherein a stiffness of the shear thickening fluid varies based on a gait speed of the user.

12. The prosthetic foot of claim 11, wherein a rod extends through the piston and is coupled to the proximal end of the second flexible member at a first end of the rod and to the attachment member at an opposite second end of the rod.

13. The prosthetic foot of claim 12, wherein the rod comprises a first portion coupled to the attachment member and a second portion coupled to the proximal end of the second flexible member.

14. The prosthetic foot of claim 12, wherein the sealed openings are configured to slidably accommodate the rod.

15. The prosthetic foot of claim 11, wherein the piston is entirely enclosed within the cylinder.

16. The prosthetic foot of claim 11, wherein the piston is partially enclosed within the cylinder, the actuator further comprising an accumulator to account for a volume change of fluid-filled space when the piston is moved relative to the cylinder.

17. The prosthetic foot of claim 11, wherein the shear thickening fluid has a higher apparent viscosity at a higher gait speed than at a lower gait speed.

18. The prosthetic foot of claim 17, wherein the shear thickening fluid has a critical shear rate between 10 s$^{-1}$ and 80 s$^{-1}$.

19. The prosthetic foot of claim 11, further comprising a third flexible member coupled to the first and second flexible members.

20. The prosthetic foot of claim 11, wherein the proximal end of the first flexible member is rotatably connected to the attachment member.

* * * * *